United States Patent [19]
Fudamoto

[11] Patent Number: 5,577,094
[45] Date of Patent: Nov. 19, 1996

[54] IRRADIATION APPARATUS WITH MOVABLE IRRADIATION HEAD

[75] Inventor: Hiroaki Fudamoto, Hyogo-ken, Japan

[73] Assignee: Mitsubishi Denki Kabushiki Kaisha, Tokyo, Japan

[21] Appl. No.: 423,050

[22] Filed: Apr. 17, 1995

[30] Foreign Application Priority Data

Jun. 30, 1994 [JP] Japan .................... 6-149774

[51] Int. Cl.⁶ ..................................... H05G 1/02
[52] U.S. Cl. ................. 378/197; 378/65; 378/195
[58] Field of Search ..................... 378/195–197, 378/65

[56] References Cited

U.S. PATENT DOCUMENTS 4,961,214  10/1990  Van Endschot et al. ............ 378/197
5,087,887   2/1992  Kawakami .

*Primary Examiner*—Craig E. Church
*Attorney, Agent, or Firm*—Rothwell, Figg, Ernst & Kurz

[57] ABSTRACT

An irradiation apparatus is provided which comprises a fixed base, an irradiation head for projecting a beam of radiation, and a support structure for the irradiation head. The support structure includes a first support carried by the base and adapted for rotation about a horizontal axis, a second support carried by the first support and adapted for rotation about an axis which extends perpendicular to the horizontal axis and intersects with the horizontal axis to define an isocenter thereat. The irradiation head is fixed to said second support. The irradiation apparatus further comprises a balancing mechanism. The balancing mechanism includes a balance weight fixedly mounted to the second support. The balance weight is positioned such that the second support, the irradiation head, and the balance weight have a center of gravity substantially coincident with the isocenter.

15 Claims, 31 Drawing Sheets

Fig. 13(a)
Fig. 13(b)
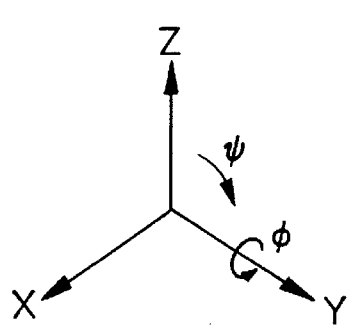
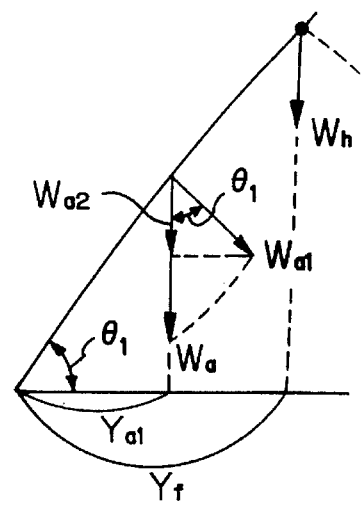
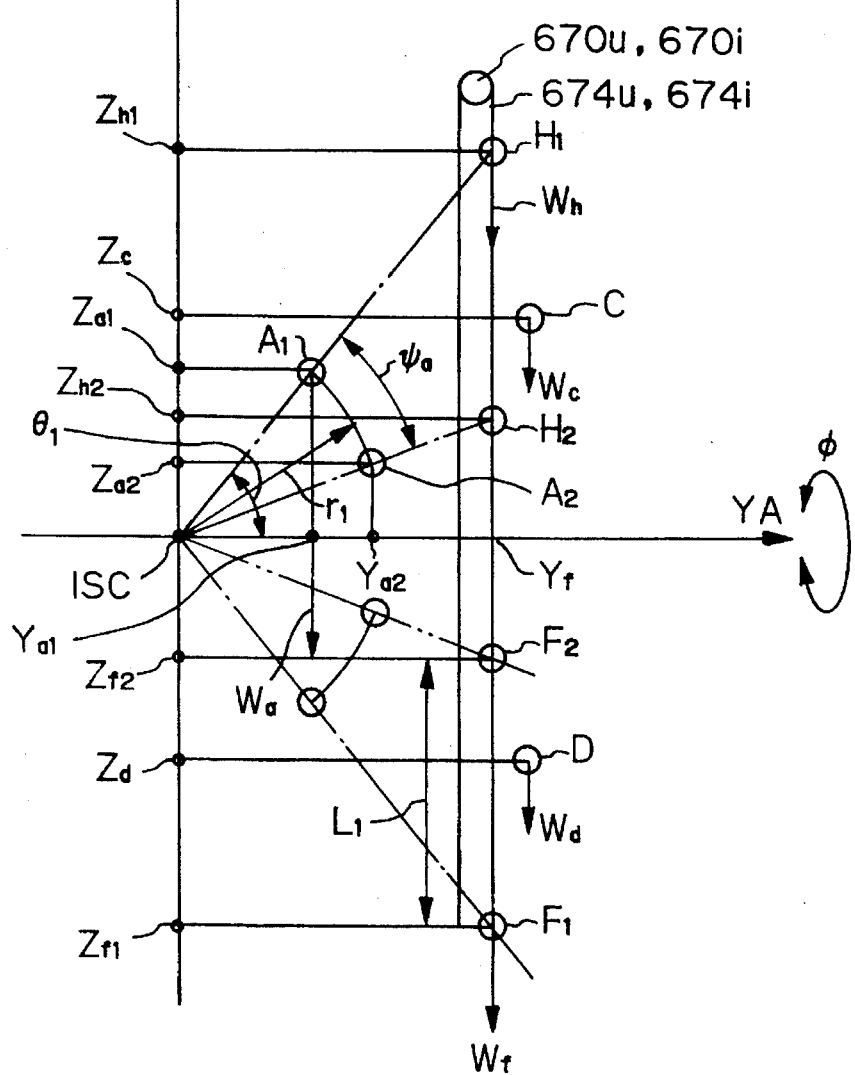

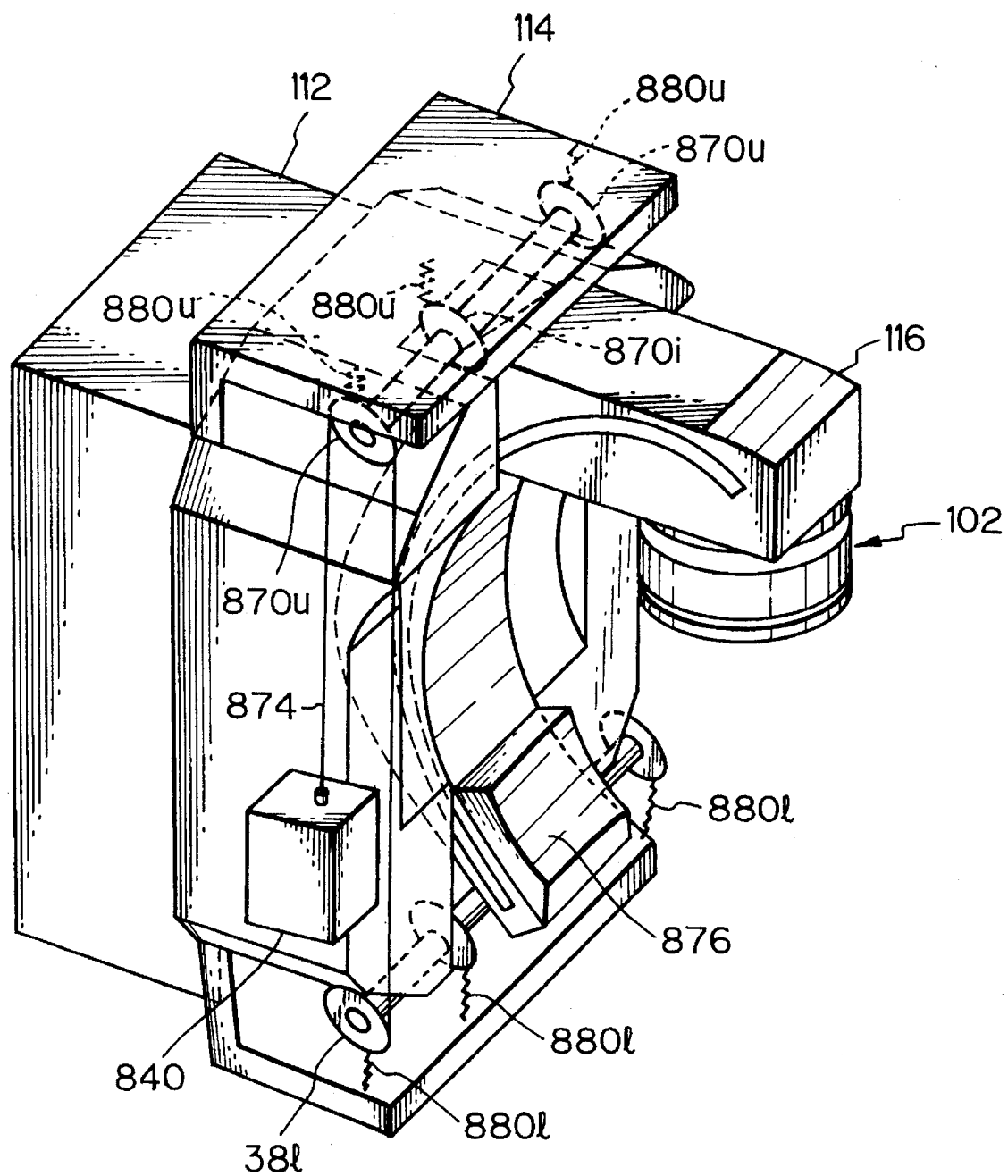

IRRADIATION APPARATUS WITH MOVABLE IRRADIATION HEAD

BACKGROUND OF THE INVENTION

1. Field of the Invention

The present invention relates to an irradiation apparatus having a movable irradiation head.

2. Description of Prior Art

There have been known various irradiation apparatuses, such as radiotherapy apparatuses and X-ray projectors, having a movable irradiation head for emitting or projecting a beam of radiation. A typical type of such irradiation apparatus has a support structure for the irradiation head, which enables a wide range of controlling of the orientation of the axis of the radiation beam emitted from the irradiation head in two-axes control. The support structure comprises a fixed base adapted to be fixed on an installation site such as a floor of a treatment room, a rotary support carried by the base for rotation about Y-axis extending horizontally, and a head support carried by the rotary support for rotation about X-axis which is fixed relative to the rotary support and extends in perpendicular to the Y-axis. The irradiation head is fixed to the head support.

In this geometry of the support structure, the intersection between the X- and Y-axes is fixed and immovable relative to the floor on which the irradiation apparatus is fixedly installed, irrespective of the rotational positions of the rotary support and the head support. Further, the irradiation head is mounted on the head support such that the axis of the radiation beam from the head passes through the intersection between the X- and Y-axes, thereby it is ensured that the radiation beam always passes through the fixed point defined by the intersection of the axes. Generally, the irradiation field in the body of a patient is positioned on this fixed point during inspection or treatment, in order to achieve the positional precision of irradiation. The fixed point, i.e. the intersection between the X- and Y-axes, is commonly referred to as "isocenter." Z-axis can be defined as one extending in perpendicular to both the X- and Y-axes and passing through the isocenter.

In general, it is desired that any moving parts should be balanced as a whole whatever positions they have been moved. For the irradiation apparatus described above, the balanced state can be achieved when the center of gravity of the head support with any parts supported thereby lies on X-axis and the center of gravity of the rotary support with any parts supported thereby lies on Y-axis.

However, because the irradiation head is typically far heavier than any other components and parts of the irradiation apparatus, an excessive imbalance tends to occur if no balancing mechanism is provided. Any excessive imbalance may i) cause an undesirable deformation of parts resulting in an inaccurate positioning of the radiation beam, ii) require drive motors and gear trains for controlling the positions of moving parts to have great capacities, and iii) allow a "free-fall" if a power failure happens and the drive motors are deenergized (the free-fall is the movement of a part or parts of the apparatus induced by the gravity, tending to lower the center of gravity of the moving parts as a whole).

There has been proposed no irradiation apparatus which is of the described type and has a balancing mechanism that provides sufficient results with simple and reliable structure.

SUMMARY OF THE INVENTION

It is therefore an object of the present invention to provide an irradiation apparatus comprising a movable irradiation head and a support structure for the irradiation head in which the support structure is provided with an improved balancing mechanism.

According to one aspect of the present invention, there is provided an irradiation apparatus which comprises: a) a fixed base; b) an irradiation head for projecting a beam of radiation; c) means for supporting said irradiation head, said means including, a first support carried by said base and adapted for rotation about a horizontal axis, a second support carried by said first support and adapted for rotation about an axis which extends perpendicular to said horizontal axis and intersects with said horizontal axis to define an isocenter thereat, said irradiation head being fixed to said second support; and d) a balance means including a balance weight fixedly mounted to said second support, said balance weight being positioned such that said second support, said irradiation head, and said balance weight have a center of gravity substantially coincident with said isocenter.

According to another aspect of the present invention, there is provided an irradiation apparatus which comprises: a) a fixed base; b) an irradiation head for projecting a beam of radiation; c) means for supporting said irradiation head, said means including: a first support carried by said base and adapted for rotation about a horizontal first axis; and a second support carried by said first support and adapted for rotation about a second axis which extends perpendicular to said first axis and intersects with said first axis to define an isocenter thereat, said irradiation head and said second support being fixed to each other so as to compose a head section; d) a balance means, said balance means comprising: a balance weight supported by said first support for rotation about said second axis; and an interlocking mechanism for keeping said second support and said balance weight in an interlocking relation; and e) said interlocking mechanism causing a rotation of said balance weight such that the center of gravity of said balance weight is maintained i) on a line passing through said isocenter and a position which is symmetrical to a position of the center of gravity of said head section with respect to said first axis, and ii) on a position establishing a balance between said balance weight and said head section, whereby said head section and said balance weight have a center of gravity substantially lying on said first axis.

According to a further aspect of the present invention, there is provided an irradiation apparatus which comprises: a) a fixed base; b) an irradiation head for projecting a beam of radiation; c) means for supporting said irradiation head, said means including: a first support carried by said base and adapted for rotation about a horizontal first axis; a second support carried by said first support and adapted for rotation about a second axis which extends perpendicular to said first axis and intersects with said first axis to define an isocenter thereat, said irradiation head and said second support being fixed to each other so as to compose a head section; and d) a balance means, said balance means comprising: a movable balance weight supported by said first support for linear motion; and an interlocking mechanism for keeping said second support and said balance weight in an interlocking relation; and e) said interlocking mechanism causing a linear motion of said balance weight such that the center of gravity of said balance weight is maintained i) on a line passing through said isocenter and a position which is symmetrical to a position of the center of gravity of said head section with respect to said first axis, and ii) on a position establishing a balance between said balance weight and said head section.

The above and other objects, features and advantages of the present invention will be apparent from the following detailed description of the preferred embodiments of the present invention, provided as only exemplary and not exclusive ones, taken in conjunction with the accompanying drawings.

BRIEF DESCRIPTION OF THE DRAWINGS

FIGS. 13(a) and 13(b) illustrate the principle of the operation of the irradiation apparatus of FIGS. 12(a) and 12(b);

FIG. 17 is an isometric view of the interlocking mechanism used in the irradiation apparatus of FIGS. 16(a) and 16(b);

DETAILED DESCRIPTION OF THE PREFERRED EMBODIMENTS

Figure 1:
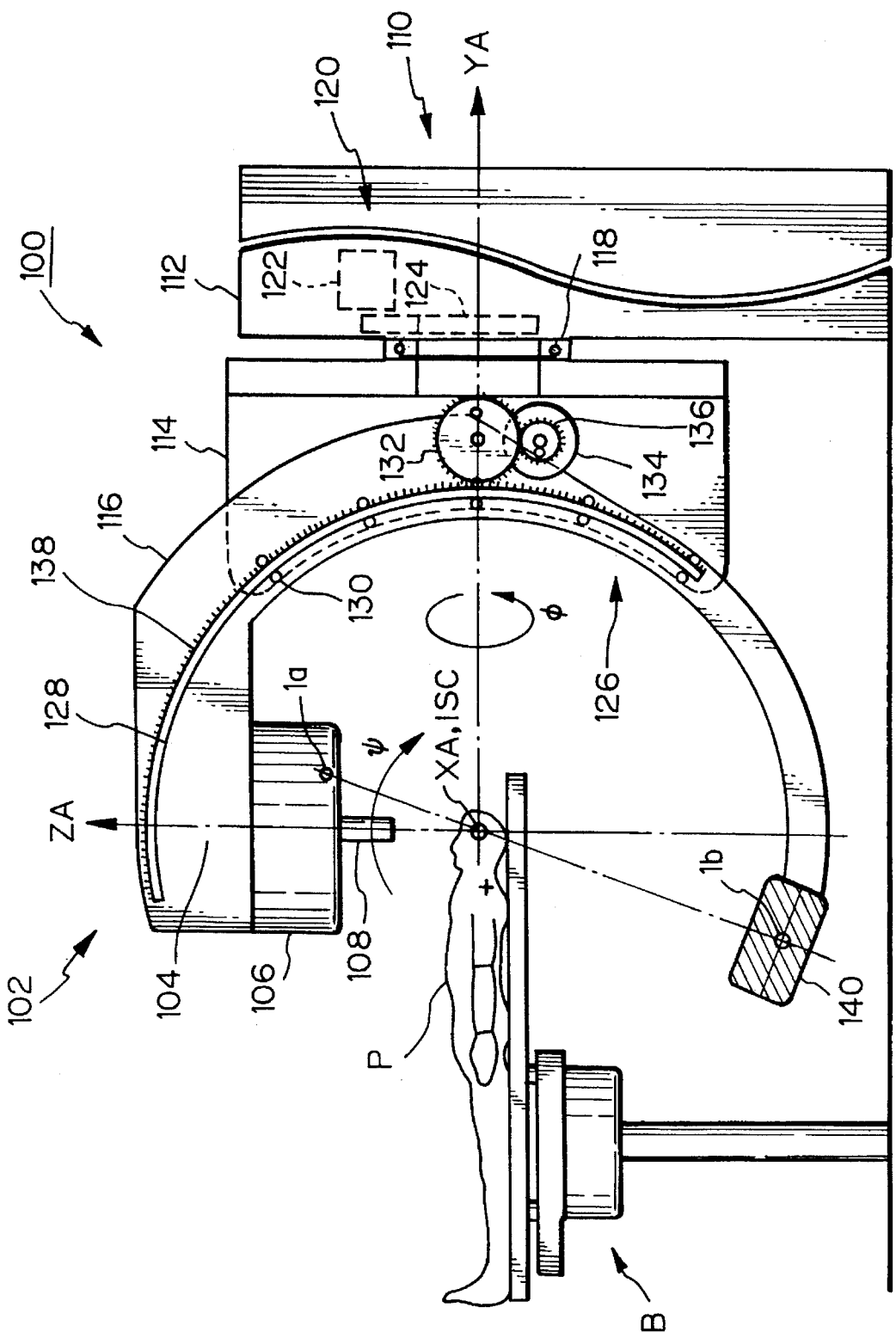
FIG. 1 is a schematic side view of an irradiation apparatus in accordance with a first embodiment of the present invention.

Referring now to the accompanying drawings, and in particular to FIG. 1, there is shown an irradiation apparatus 100 according to a first embodiment of the present invention. The irradiation apparatus 100 comprises an irradiation head 102 for emitting or projecting a beam of radiation and a support structure 110 for the irradiation head 102. The support structure 110 enables a wide range of controlling of the orientation of the axis of the radiation beam emitted from the irradiation head 102 in two-axes control. In accordance with the present invention, the support structure 110 is provided with a balancing mechanism as detailed below.

The irradiation head 102 comprises a radiation generator 104 such as an X-ray generator, a radiation beam collimator 106 such as an X-ray collimator, and a radiation applicator 108 such as an X-ray applicator through which a narrow beam of an X-ray beam is projected to an irradiation field in the body of a patient P lying on a bed B. This is merely a specific example, and any other irradiation head may be used as well.

The support structure 110 comprises a fixed base 112 adapted to be fixed on an installation site such as a floor of a treatment room, a rotary support (first support) 114 carried by the base 112 for rotation about Y-axis YA extending horizontally, and a head support (third support) 116 carried by the rotary support 114 for rotation about X-axis XA which is fixed relative to the rotary support 114 and extends in perpendicular to the Y-axis YA. The irradiation head 102 is fixed to the head support 116.

Importantly, the Y-axis YA is fixed or immovable relative to the base 112 fixedly installed such as on a floor of a treatment room, while the X-axis XA is movable or swingable relative to the base 112 with keeping the perpendicular relationship to the Y-axis YA. The X- and Y-axes intersect with each other at a fixed point irrespective of the rotational or angular positions of the rotary support 114 and the head support 116, the fixed point being referred to as the isocenter as previously mentioned, which will be described in more detail below.

The rotary support 114 is a rigid, generally gate-shaped member. The rotary support 114 is rotatably carried by the base 112 via a bearing unit 118 and controllably driven for rotation by means of a first drive mechanism 120 comprising an electric motor 122 mounted on the base 112 and a suitable gear train 124 drivingly connecting the output shaft of the motor 122 to the rotary support 114. The motor 122 is controlled by a central control unit (not shown), which may be of any known type and contained in the base 112.

The head support 116 is a rigid, generally C-shaped member with the irradiation head 102 fixedly connected on its one end (the upper end in the illustrated position). The head support 116 is rotatably supported on the rotary support 114 via a guide structure 126 comprising a pair of arcuate guide rails 128 fixed on respective sides of the head support 116 and two sets of guide rollers 130 mounted on the rotary support 114. Each set of guide rollers 130 cooperate with one of the guide rails 126 to support that guide rail while allowing free movement of that guide rail along an imaginary circle on which the arcuate guide rail lies. In this manner, the head support 116 is supported for rotation about the axis passing through the center of and extending at right angle relative to the imaginary circle. This axis is the X-axis AX mentioned above. The guide structure 126 is arranged such that the X-axis XA should intersects with the Y-axis at right angle.

In this geometry of the support structure 110, the intersection ISC between the X- and Y-axes is fixed and immovable relative to the floor on which the irradiation apparatus 100 is fixedly installed, irrespective of the rotational positions of the rotary support 114 and the head support 116. Further, the irradiation head 102 is mounted on the head support 116 such that the axis of the radiation beam from the head 102 passes through the intersection ISC between the X- and Y-axes, thereby it is ensured that the radiation beam always passes through the fixed point defined by the intersection of the axes. Generally, the irradiation field in the body of a patient is positioned on this fixed point during inspection or treatment, in order to achieve the positional precision of irradiation. The fixed point, i.e. the intersection between the X- and Y-axes, is commonly referred to as "isocenter." Z-axis ZA can be defined as one extending in perpendicular to both the X- and Y-axes and passing through the isocenter ISC.

The head support 116 is controllably driven for rotation by means of a second drive mechanism 132 comprising an electric motor 134 mounted on the rotary support 114 and a suitable gear train 136 drivingly connecting the output shaft of the motor 134 to the head support 116, the gear train 136 including an arcuate rack 138 which is fixedly mounted on the head support 116, positioned on an imaginary circle centered to the isocenter ISC and has teeth on its radially outer side. The motor 134 is controlled by the central control unit mentioned above (not shown).

The orientation of irradiation, i.e. the angular position of the axis of the radiation beam projected from the irradiation head 102, may be set in various desired orientations by controlling the motors 122 and 134 of the first and second drive mechanism 120 and 132 to establish appropriate rotational positions of the rotary support 114 and the head support 116 about the X- and Y-axes, respectively.

As mentioned above, the support structure 110 is provided with a balancing mechanism, which will be described in detail hereinafter. In general, it is desired that any moving parts should be balanced as a whole whatever positions they have been moved. For the irradiation apparatus 100, the balanced state can be achieved when the center of gravity of the head support 116 with any parts supported thereby lies on the X-axis and the center of gravity of the rotary support 114 with any parts supported thereby lies on the Y-axis. However, because the irradiation head is typically far heavier than any other components and parts of the irradiation apparatus of the above described type, an excessive imbalance would occur if no balancing mechanism is provided. Any excessive imbalance may i) cause an undesirable deformation of parts resulting in an inaccurate positioning of the radiation beam, ii) require the drive motors and the gear trains for controlling the positions of moving parts to have great capacities, and iii) allow a "free-fall" in the event of a power failure casing the drive motors to be deenergized (the free-fall is the movement of a part or parts of the apparatus induced by the gravity, tending to lower the center of gravity of the moving parts as a whole).

The balancing mechanism may be formed in various configurations. In the embodiment shown in FIG. 1, the balancing mechanism comprises a balance weight 140 fixedly mounted on the head support 116 at the lower end thereof remote from the irradiation head 102. The center of gravity of the combination of the irradiation head 102 and the rotary support 114 is shown in FIG. 1 at 1$a$, and the center of gravity of the balance weight 140 is shown at 1$b$. The position of 1$b$ is selected such that: 1) 1$b$ should lie on a line passing through 1$a$ and the isocenter ISC; and 2) the distance Db between 1$b$ and ISC should be related to the distance Da between 1$a$ and ISC as follows.

$$Db = Da \times 1a/1b$$

By this positioning of the balance weight 140, the head support 116, the irradiation head 102 and the balance weight 140 have a center of gravity substantially coincident with the isocenter ISC irrespective of the rotational or angular positions of the head support 116 about the X-axis XA.

Figure 2:
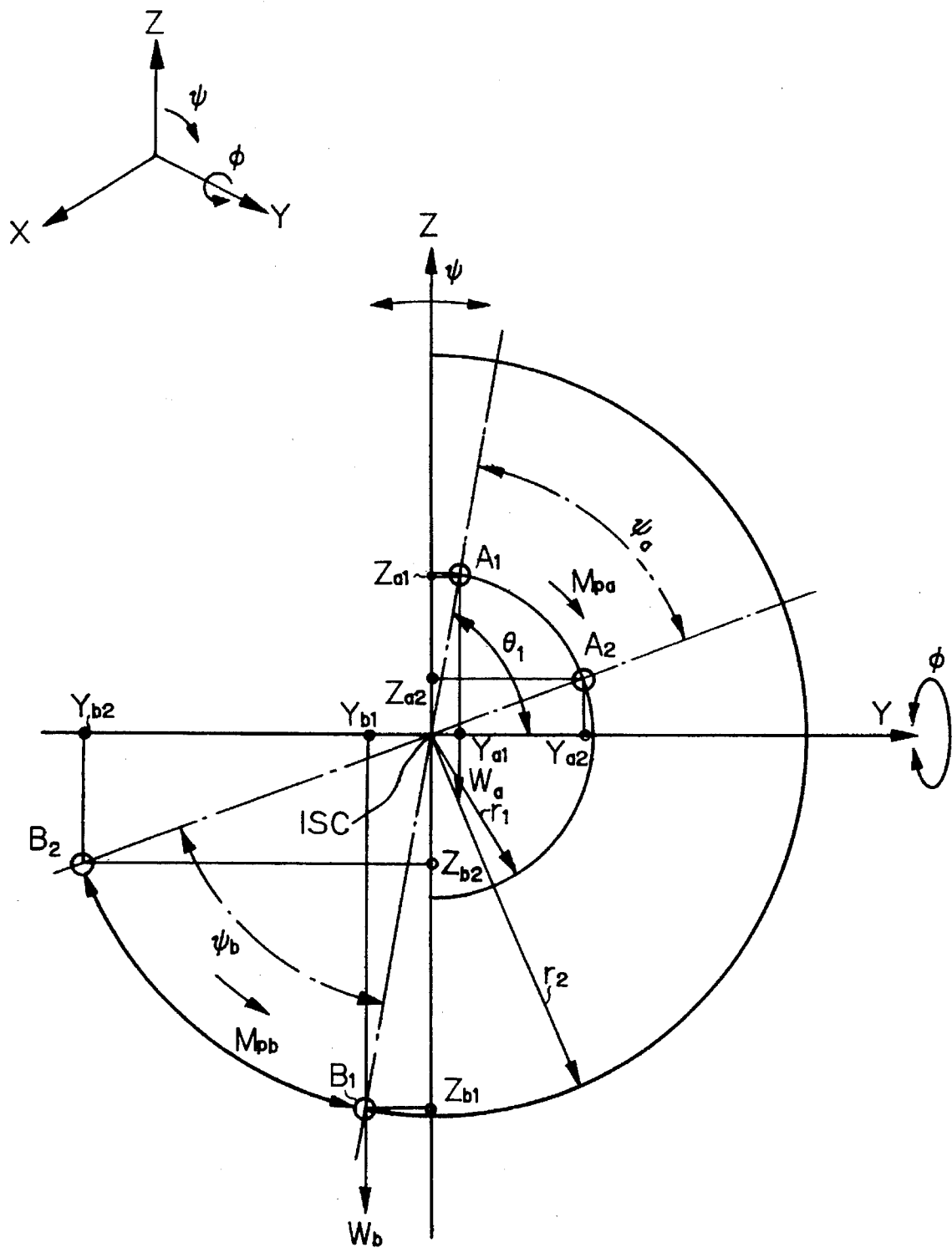
FIG. 2 illustrates the principle of the operation of the irradiation apparatus of FIG. 1.

Referring now to FIG. 2, the operation of the irradiation apparatus 100 will be described in detail.

In FIG. 2, ISC represents the isocenter, Wa represents the total weight of the combination of the head support 116 and the irradiation head 102, Wb represents the weight of the balance weight 140, $\psi$a represents the rotational displacement of the head support 116 in the $\psi$-direction, $\psi$b represents the rotational displacement of the balance weight 140 in the $\psi$-direction, A1 represents the initial position of the center of gravity of the combination of the head support 116 and the irradiation head 102, A2 represents the position of the center of gravity of the combination of the head support 116 and the irradiation head 102 when the former has been rotated by $\psi$ from the initial position, B1 represents the initial position of the center of gravity of the balance weight 140, and B2 represents the position of the center of gravity of the balance weight 140 when it has been rotated by $\psi$ from the initial position. The position of A1 is designated by (Ya1, Za1) and the position of A2 is designated by (Ya2, Za2). The position of B1 is designated by (Yb1, Zb1) and the position of B2 is designated by (Yb2, Zb2). $\theta$1 represents the angle of the initial position A1 of the center of gravity 1$a$ of the combination of the head support 116 and the irradiation head 102 measured from the Y-axis, r1 represents the radius of the rotation in the $\psi$-direction of the center of gravity 1$a$ of the combination of the head support 116 and the irradiation head 102, and r2 represents the radius of the rotation in the ψ-direction of the center of gravity 1b of the balance weight 140.

The total weight Wa of the combination of the head support 116 and the irradiation head 102 (this combination is referred to as "head section" hereinafter) is rotated from the initial position A1 (at the initial angle θ1) with the radius r1 by the rotational displacement ψa into the position A2. During this rotation, the center of gravity of the balance weight 140, which is mounted on the head support 116 such that its center of gravity occupies the position that is symmetrical to the position of the center of gravity of the head section with respect to the isocenter ISC, is rotated from the position B1 into the position B2. The rotation balance in this rotational motion will be described hereinafter.

First, the balance for the rotation in the Φ-direction is described. The rotation momentum of the weight Wa of the head section effecting on the Y-axis YA when the head section rotates in the Φ-direction, as designated by Ma1, is the product of the total weight Wa of the head section and Z-coordinate Za1 of the initial position A1 of the head section and thus expressed as $$Ma1=Wa \times Za1.$$

Similarly, the rotation momentum of the total weight Wb of the balance weight 140 effecting on the Y-axis YA when the balance weight 140 is at the position B1, as designated by Mb1, is expressed as $$Mb1=Wb \times Zb1.$$

In order to balance Ma1 with Mb1, Ma1 should be equal to Mb1. This is achieved by positioning the balance weight weighing Wa at any position having its Z-coordinate of Zb1, where $$Wb=Wa \times Za1/Zb1=Wa \times r1/r2. \quad (1)$$

This is the initial position of the irradiation apparatus 100.

Next, let us consider the balance about the ψ-axis under this situation and when the center of gravity of the head section has been rotated by the rotational displacement ψa. The balance weight 140 will be rotated by the same rotational displacement ψa in the ψ-direction, thus $$\psi1=\psi2.$$

The Z-coordinate Za2 of the position A2 of the center of gravity of the head section when the head section has been rotated by ψa is expressed as $$Za2=r1 \times \sin(\theta1-\psi a),$$

so that the rotation momentum Ma2 of the head section effecting on the X-axis is expressed as $$Ma2=Wa2=Wa \times r1 \times \sin(\theta1-\psi a).$$

Similarly, the rotational momentum Mb2 of the weight Wb of the balance weight 140 effecting on the Y-axis when the balance weight 140 is at the position B2 is expressed as $$Mb2=Wb \times Zb2=-(Wb \times r2 \times \sin(\theta1-\psi a)).$$

This together with E. (1) results in $$Mb2=-(Wa \times r1 \times \sin(\theta1-\psi a)),$$

meaning that the rotational balance about Y-axis is always established irrespective of the rotational positions of the head section in the ψ-direction.

Next, let us consider the balance about the X-axis. Whatever positions the head section occupies, the rotation momentum MPa of the center of gravity of the head section effecting on the X-axis is expressed as $$MPa=Wa \times r1$$

and the rotation momentum MPb of the weight Wb of the balance weight 140 effecting on the X-axis is expressed as $$MPb=Wb \times r2.$$

Form E. (1) we have $$Wb=Wa \times r1/r2$$

thus $$MPb=Wa \times r1.$$

The direction of the rotational momentum MPa and that of the rotational momentum MPb are always opposite to each other so that the rotational balance about the X-axis will be established whatever positions the head section occupies.

Thus, according to the irradiation apparatus 100 of the first embodiment, the center of gravity of the combination of the balance weight 140 and the head section (the latter is in turn the combination of the head support 116 and the irradiation head 102) is coincident with the isocenter ISC, so that both the balances for the rotation in the ψ-direction and the rotation in the Φ-direction will be established irrespective of the rotational positions of the head section in the ψ-direction. By virtue of this, the tendency of the irradiation head 102 to free-fall in the rotational direction of ψ is reduced, and only small capacities are required for the motors 122 and 134 and the gear trains 124 and 136 to drive the head section for rotations in the Φ and ψ-directions so that they may be of relatively light weight.

FIGS. 3 to 31 show various irradiation apparatuses according to further embodiments of the present invention. These irradiation apparatuses are the same in structure and function with the first embodiment of FIG. 1 described above, except that their balancing mechanisms have different configurations. Thus, in the following description, only the balancing mechanism of each irradiation apparatus will be described for simplicity, with like components being indicated by like reference numerals throughout the drawings.

Figure 3:
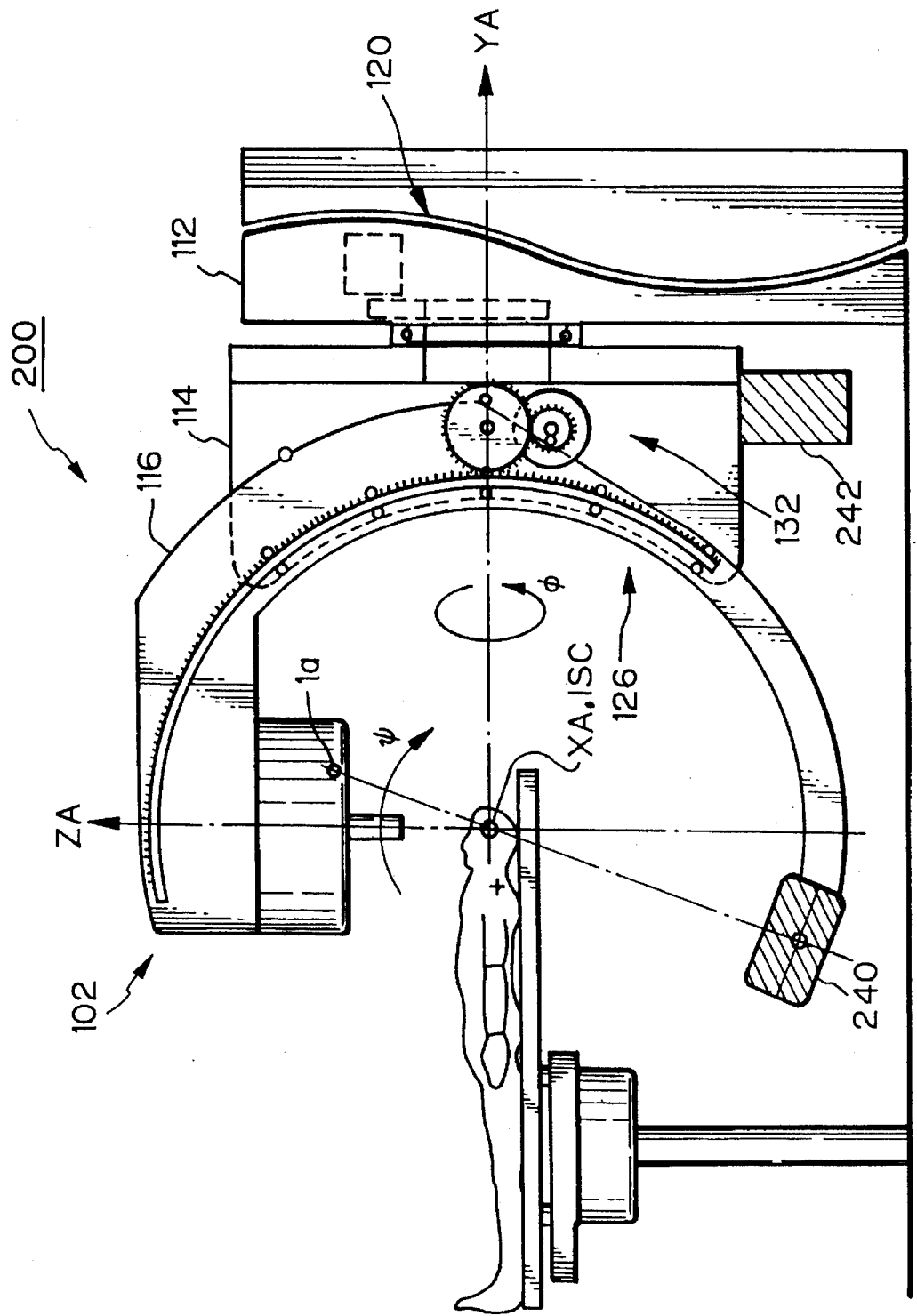
FIG. 3 is a schematic side view of an irradiation apparatus in accordance with a second embodiment of the present invention.
Figure 4:
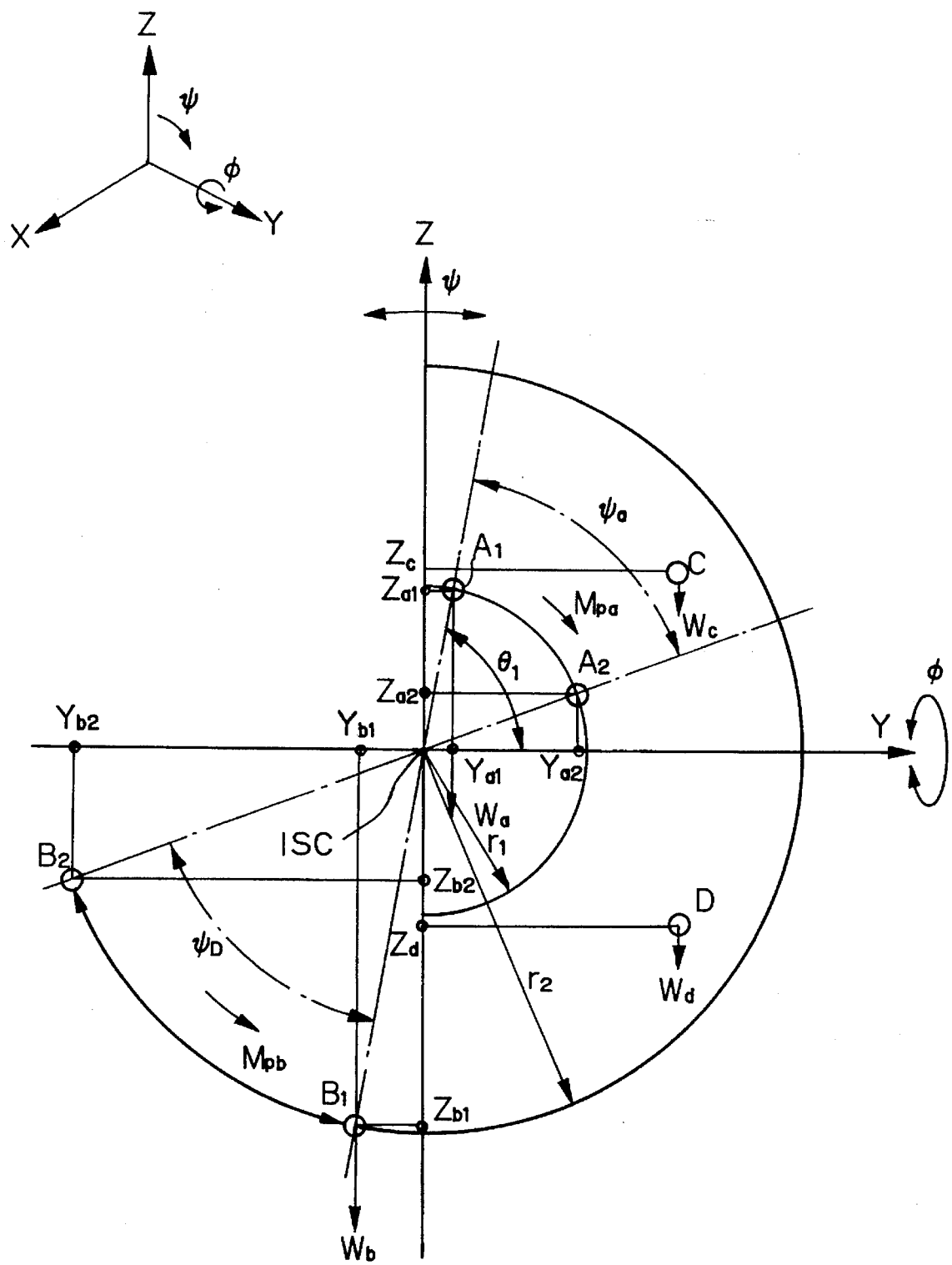
FIG. 4 illustrates the principle of the operation of the irradiation apparatus of FIG. 3.

FIGS. 3 and 4 show an irradiation apparatus 200 according to a second embodiment of the present invention. The irradiation apparatus 200 has a balancing mechanism comprising a first balance weight 240 and a second balance weight 242. The first balance weight 240 has its weight and positioning selected in the same manner as the balance weight 140 used in the embodiment of FIG. 1 and thus has the same function as the balance weight 140. The second balance weight 242 is fixedly mounted on the rotary support 114 and serves to make the rotary support balanced with respect to the Y-axis YA by keeping the center of gravity of the combination of the rotary support 114 and any parts supported thereon to lie on the Y-axis irrespective of the rotational positions of the rotary support 114 about the Y-axis YA.

Referring now to FIG. 4, the operation of the irradiation apparatus 200 will be described in detail. In FIG. 4, the designations Wa, Wb, ψa, ψb, A1, A2, B1, B2, θ1, r1, r2, Ya1, Ya2, Yb1, Yb2, Za1, Za2, Zb1 and Zb2 represent the same things as they do in connection with the first embodiment, as shown in FIG. 2. Additionally, Wc represents the total weight of the rotary support 114, Wd represents the weight of the second balance weight 242, C represents the position of the center of gravity of the rotary support 114, D represents the position of the center of gravity of the second balance weight 242, Zc represents the Z-coordinate of the position C and Zd represents the Z-coordinate of the position D.

The balances for the rotation in the Φ-direction and the rotation in the ψ-direction of the head section (comprising the head support 116 and the irradiation head 102) are the same as with the first embodiment. On the other hand, the rotation momentum Mc of the total weight Wc of the rotary support 114 effecting on the Y-axis when the head section is at any ψ position and the rotary support 114 is rotated in the Φ-direction is expressed as $$Mc = Wc \times Zc,$$

and the rotation momentum Md of the weight Wd of the second balance weight 242 effecting on Φ-axis is expressed as $$Md = Wd \times Zd.$$

By selecting the weight Wd of the second balance weight 242 to be $$Wd = Wc \times Zc / Zd$$

we have $$Mc = Md$$

meaning that the balance for the rotation about the Y-axis of the rotary support 114 will be completely achieved.

Thus, according to the irradiation apparatus 200 of the second embodiment, irrespective of the positions the head section, the balances for the rotation in the Φ-direction and the rotation in the ψ-direction of the total weight of the head section and the weight of the first balance weight 140 is maintained, and the balance state for the rotation in the Φ-direction of the rotary support 116 is maintained by the second balance weight 242, so that any rotational balance with respect to the rotating parts of the irradiation apparatus 200 may be achieved. Further, by virtue of this, only small capacities are required for the motors 122 and 134 and the Gear trains 124 and 136 to drive the head section for rotations in the Φ- and ψ-directions so that they may be of relatively light weight.

Figure 5:
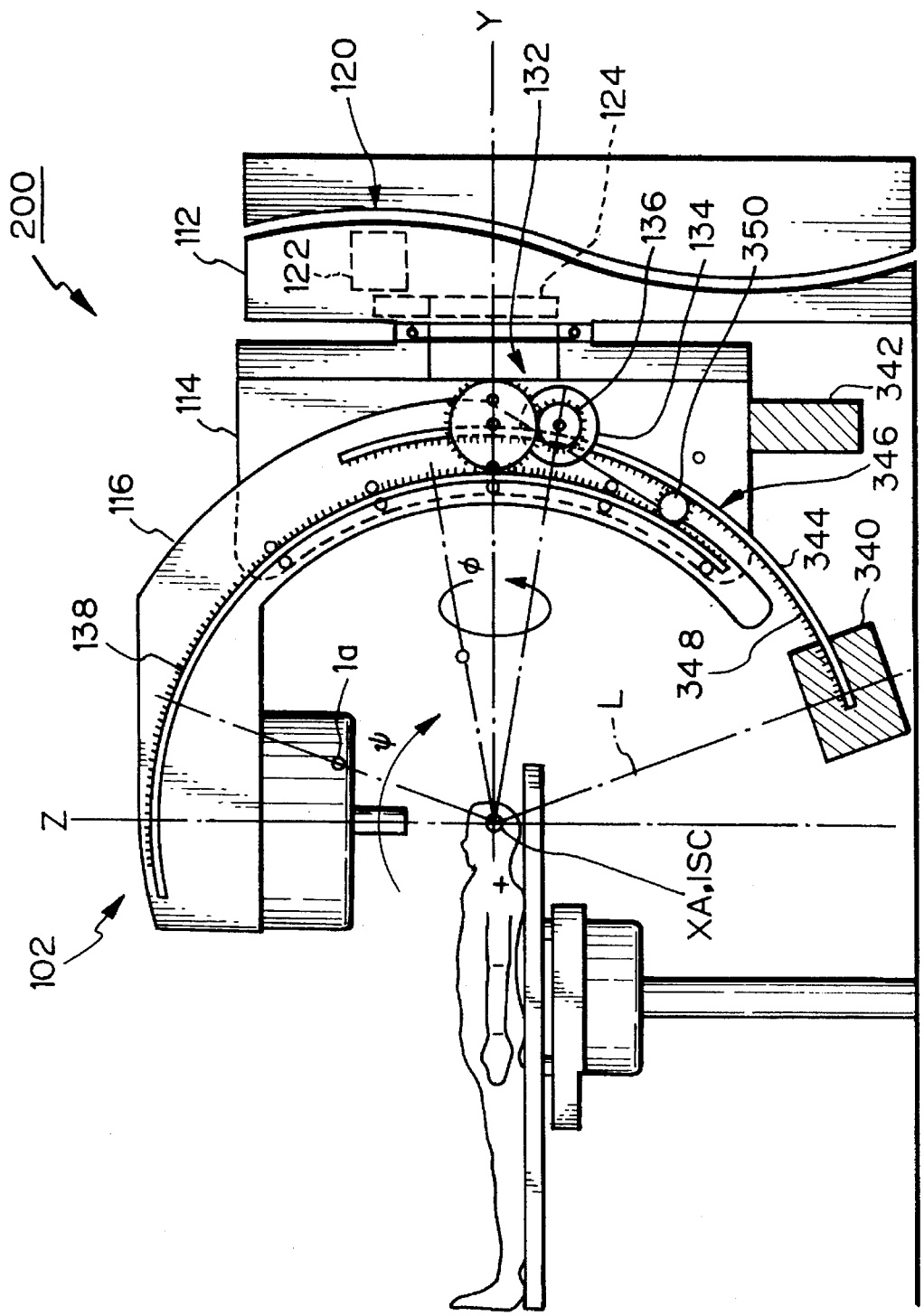
FIG. 5 is a schematic side view of an irradiation apparatus in accordance with a third embodiment of the invention.
Figure 6:
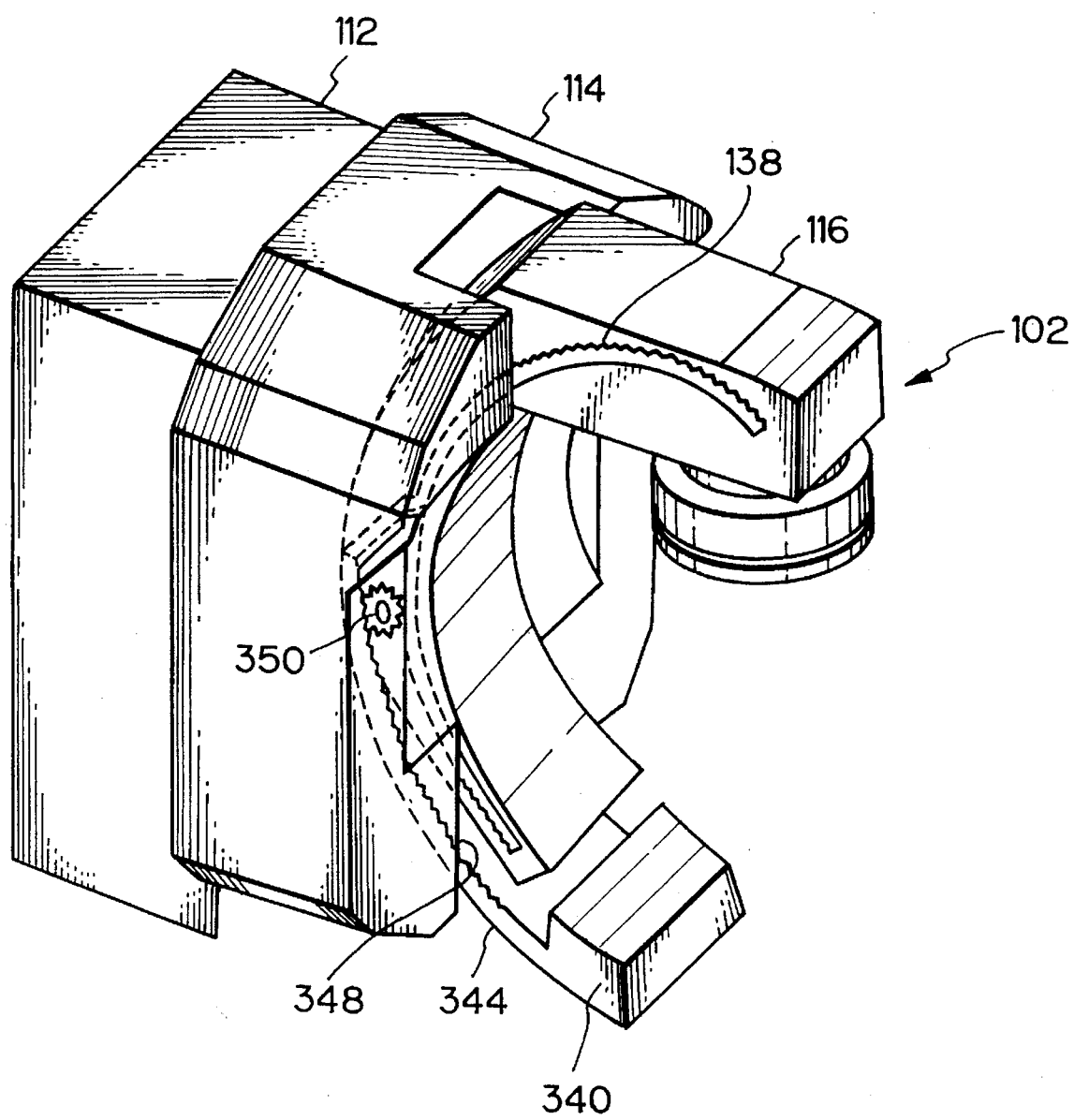
FIG. 6 is an isometric view of the interlocking mechanism used in the irradiation apparatus of FIG. 5.
Figure 7:
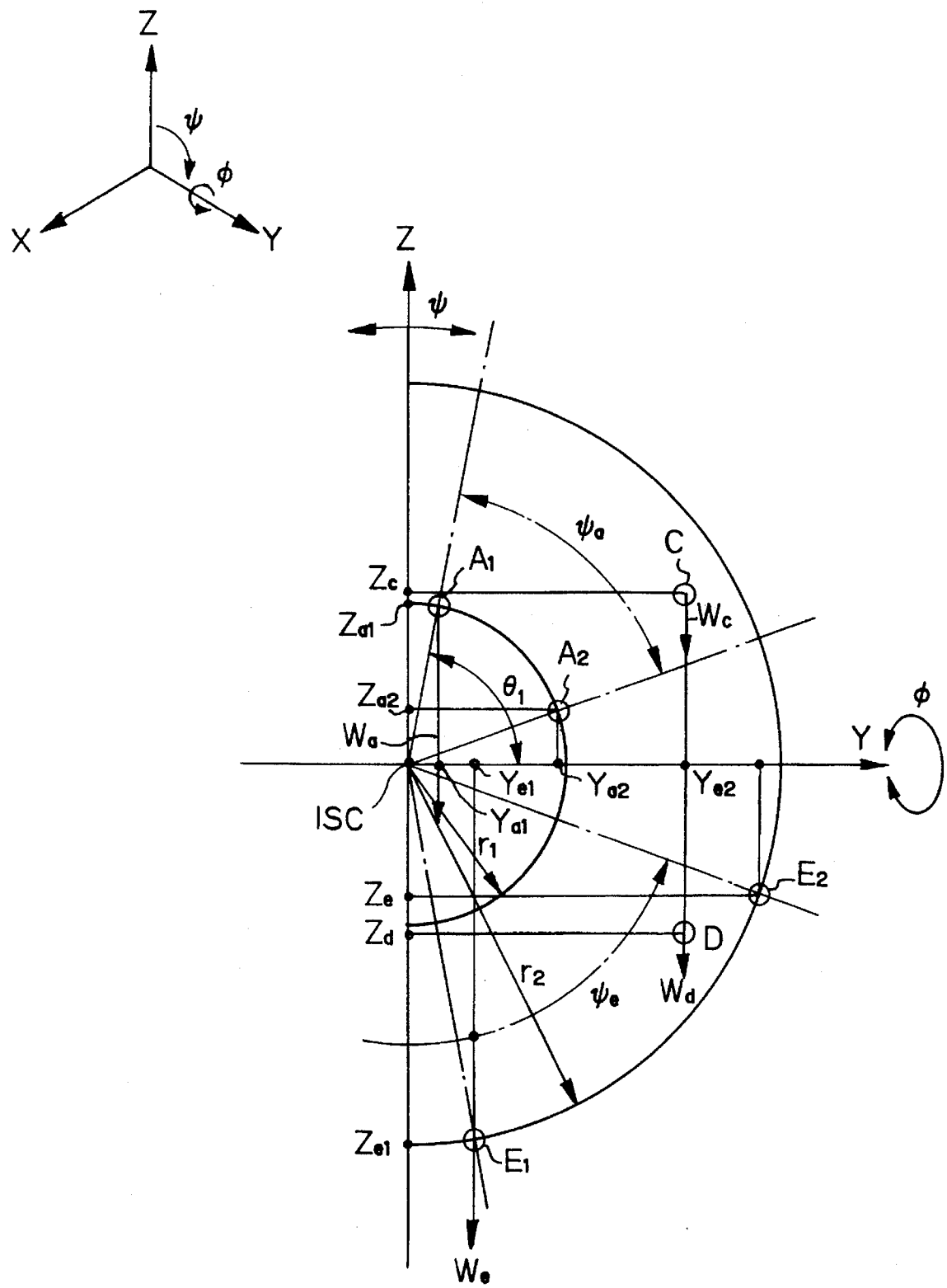
FIG. 7 illustrates the principle of the operation of the irradiation apparatus of FIG. 5.

FIGS. 5 to 7 show an irradiation apparatus 300 according to a third embodiment of the present invention. The irradiation apparatus 300 has a balancing mechanism comprising a first balance weight 340 and a second balance weight 342. The second balance weight 342 is fixedly mounted on the rotary support 114 and has the same function and effect as the second balance weight 242 of the second embodiment, that is, it serves to make the rotary support 114 balanced. The first balance weight 340 is attached to a balance weight support 344 which is supported on the rotary support 114 for rotation about the X-axis XA via a second guide structure 346 which is similar in arrangement and function to the guide structure 126 used for supporting the head support 116 on the rotary support 114 for rotation about the X-axis.

The balancing mechanism comprises an interlocking mechanism for keeping the balance weight support 344 and the head support 116 in an interlocking relation with each other. In this embodiment, the interlocking mechanism is a gear type transmission mechanism comprising an arcuate rack 348 and a pinion 350. The rack 348 is fixedly mounted on the balance weight support 344, positioned on an imaginary circle centered to the isocenter ISC and has teeth on its radially inner side. The pinion 350 is mounted on the rotary support 114 for rotation and engages both the arcuate rack 138 on the head support 116 and the arcuate rack 348 on the balance weight support 344.

By virtue of the provision of this interlocking mechanism, any rotation of the head support 116, caused by the drive motor 134, about the X-axis in one direction by a certain angle will cause the corresponding rotation of the balance weight support 344 about the X-axis in the opposite direction by nearly the same angle. In the initial position as shown in FIG. 5, the center of gravity 1b of the combination of the balance weight support 344 and the first balance weight 340 (this combination is referred to as "balance weight section" hereinafter) is positioned: a) on a line L passing through the isocenter ISC and a point SP which is symmetrical to the center of gravity 1a of the head section with respect to the Y-axis; and b) at such distance from the Y-axis that makes the balance weight section and the head section balanced with respect to the Y-axis.

In operation, the motor 122 drives the rotary support 114 through the gear train 124 to rotate it in the Φ-direction, thereby rotating the head support 116 with the irradiation head 102, the balance weight support 344 with the first balance weight 340, and the second balance weight 342 in the Φ-direction as well.

Regarding the rotation of the irradiation head 102 in the ψ-direction, the motor 134 drives the head section through the gear train 136 to rotate it in the ψ-direction, when the balance weight section is rotated through the interlocking mechanism in the opposite direction to the head section.

Referring now to FIG. 7, the balancing relationship in the above operation of the irradiation apparatus 200 will be described in detail. In FIG. 7, the designations Wa, Wb, Wc, Wd, ψa, A1, A2, C, D, θ1, r1, r2, Ya1, Ya2, Za1, Za2, Zc and Zd represent the same things as they do in connection with the second embodiment, as shown in FIG. 4. Additionally, E1 represents the initial position of the center of gravity of the balance weight section and E2 represents the position of the center of gravity of the balance weight section when it has been rotated by ψe. The position E1 is designated by (Ye1, Ze1) and the position E2 is designated by (Ye2, Ze2).

Suppose that the weight Wa of the head section (comprising the head support 116 and the irradiation head 102) is rotated from the initial position A1 (at the initial angle θ1), with the radius r1, by the rotational displacement ψa, into the position A2. During this rotation, the weight We of the balance weight section (comprising the balance weight support 344 and the first balance weight 340), whose center of gravity occupies the position which is symmetrical to the position of the center of gravity of the head section with respect to the Y-axis, is rotated from the position E1 into the position E2, by the rotational displacement ψe which is the same in magnitude as ψ but in opposite direction to that of the head section. The rotation balance in this rotational motion will be described hereinafter.

The rotation momentum of the weight Wa of the head section effecting on the Y-axis YA when the head section rotates in the Φ-direction, as designated by Ma1, is the product of the weight Wa of the head section and Z-coordinate Za1 of the initial position A1 of the head section and thus expressed as $$Ma1 = Wa \times Za1.$$

Similarly, the rotation momentum of the weight We of the balance weight section effecting on the Y-axis YA when the balance weight section is at the position E1, as designated by Me1, is expressed as $$Me1=We \times Ze1.$$

In order to balance Ma1 with Me1, Ma1 should be equal to Me1. This is achieved by positioning the balance weight section weighing We at any position having its Z-coordinate of Ze1, where $$We=Wa \times Za1/Ze1=Wa \times r1/r2. \quad (2)$$

This is the initial position of the irradiation apparatus 200. Let us consider the balance about the ψ-axis under this situation and when the center of gravity of the head section has been rotated by the rotational displacement ψa. The balance weight section will be rotated by the same rotational displacement ψa in the ψ-direction, thus $$\psi a=\psi e \text{ (}\psi e \text{ has the opposite direction).}$$

The Z-coordinate Za2 of the position A2 of the center of gravity of the head section when the head section has been rotated by ψa is expressed as $$Za2=r1 \times \sin(\theta 1-\psi a),$$

so that the rotation momentum Ma2 of the head section effecting on the X-axis is expressed as $$Ma2=Wa2=Wa \times r1 \times \sin(\theta 1-\psi a).$$

Similarly, the rotational momentum Me2 of the weight We of the balance weight section effecting on the Y-axis when the balance weight section is at the position E2 is expressed as $$Me2=We \times Ze2=-(We \times r2 \times \sin(\theta 1-\psi a).$$

This together with E. (2) results in $$Me2=-(Wa \times r1 \times \sin(\theta 1-\psi a)$$

meaning that the rotation balance about Y-axis is always established irrespective of the rotational positions of the head section in the ψ-direction.

Thus, according to the irradiation apparatus 300 of the third embodiment, irrespective of the rotational positions in the ψ-direction of the head section, the balances for the rotation in the Φ-direction and the rotation in the ψ-direction will be achieved since the center of gravity of the combination of the weight of the head section and the weight of the balance remains on the Y-axis. Thus, the tendency of the irradiation head 102 to free-fall in the rotational direction of ψ is reduced, and only small capacities are required for the motors 122 and 134 and the gear trains 124 and 136 to drive the head section for rotations in the Φ- and ψ-directions so that they may be of relatively light weight. Further, since the first balance weight 340 moves in the opposite direction to the head support 114 with respect to the rotation in the ψ-direction, any interference between the first balance weight 340 and the bed for a patient can be avoided.

Figure 8:
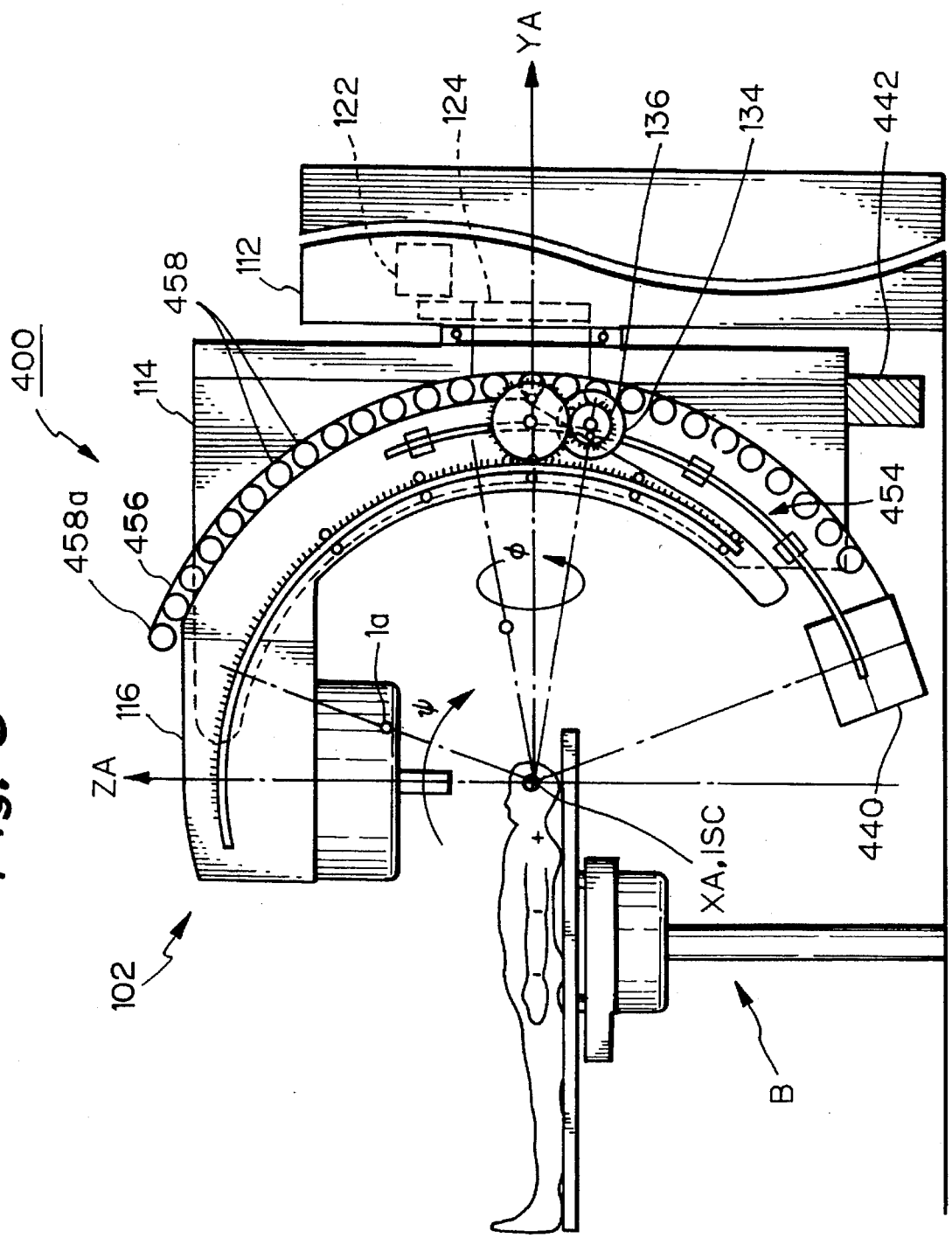
FIG. 8 is a schematic side view of an irradiation apparatus in accordance with a fourth embodiment of the present invention.
Figure 9:
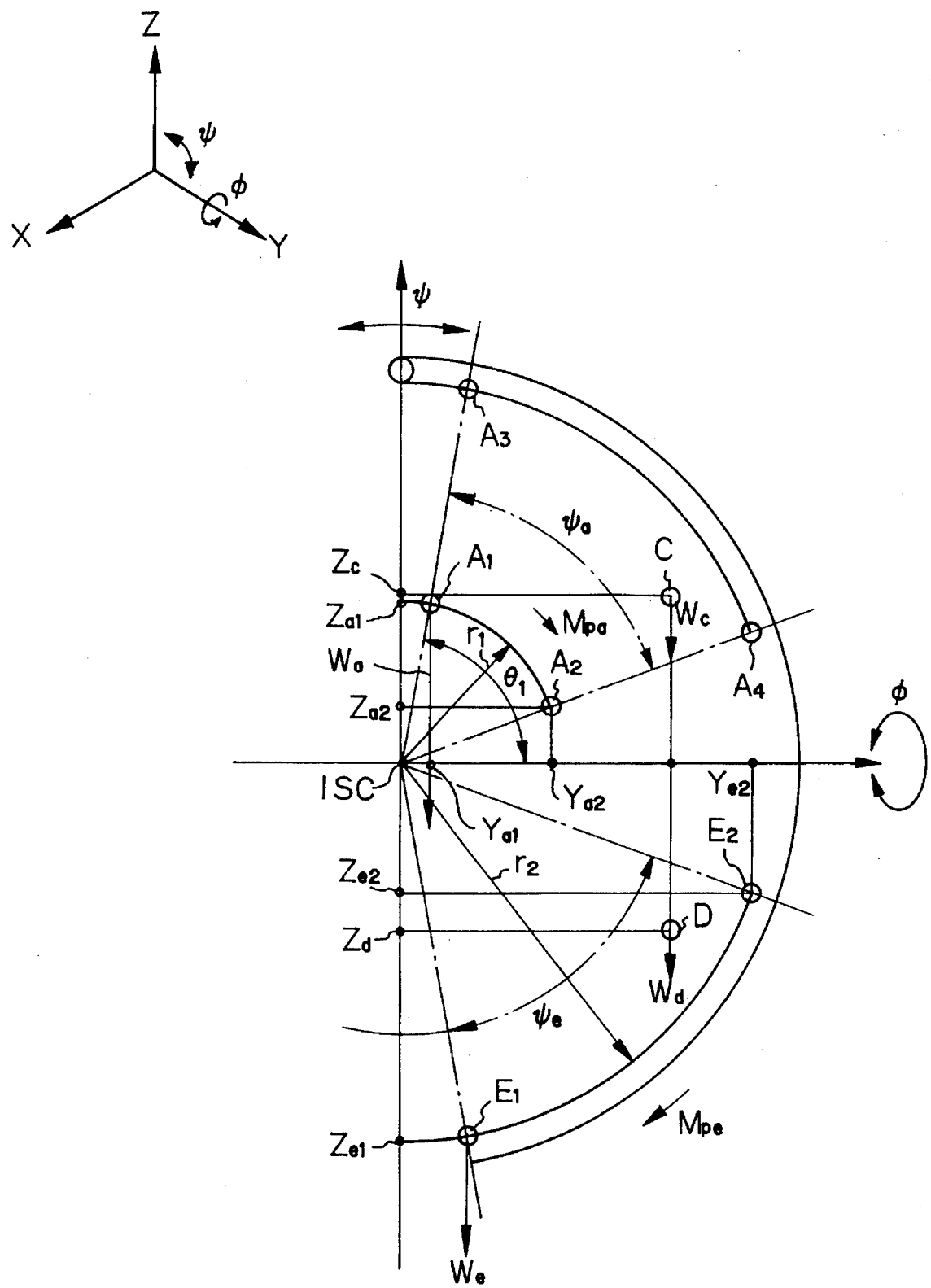
FIG. 9 illustrates the principle of the operation of the irradiation apparatus of FIG. 8.

FIGS. 8 and 9 show an irradiation apparatus 400 according to a fourth embodiment of the present invention. The irradiation apparatus 400 has a balancing mechanism comprising a first balance weight 440 and a second balance weight 442. The second balance weight 442 is fixedly mounted on the rotary support 114 and has the same function and effect as the second balance weight 242 of the second embodiment, that is, it serves to make the rotary support 114 balanced. The first weight 440 is attached to a balance weight support 454 which is supported on the rotary support 114 for rotation about the X-axis XA via a second guide structure with guide rails, which is similar in arrangement and function to the guide structure used for supporting the head support 116 on the rotary support 114 for rotation about the X-axis, except that slide bearings are used in place of the guide rollers.

The balancing mechanism comprises an interlocking mechanism for keeping the first weight support 454 and the head support 116 in an interlocking relation with each other. In this embodiment the interlocking mechanism is a wire cable type transmission mechanism comprising a length of wire cable 456 and a series of pulleys 458 mounted on the rotary support 114 along an imaginary circle centered to the X-axis XA. The wire cable 456 is trained on and guided by the pulleys 458, and has its lower end connected to the first balance weight 440 and its upper end turning down around the top pulley 458a and connected to the head support 116 at the position lower than the top pulley 458a by a certain distance. In this arrangement, the wire cable 456 is normally kept under the tension by the weights of the head support section and the balance weight section.

Referring now to FIG. 9, the operation will be described. In FIG. 9, A3 represents the position fixed relative to the head support 114, which lies on a line passing through a) the isocenter ISC and b) the initial position A1 of the center of gravity of the head section and is at a distance r2 from the isocenter ISC. A4 represents the position into which the position A3 has been moved through the rotation of the center of gravity of the head section by ψ1 from A1 into A2.

Although the first balance weight 440 moves along the guide rails of the second Guide structure unlike the third embodiment above, as long as the rotation in the Φ-direction is concerned, both the motions of the first balance weight 440 and the head support 114 are the same as those of the third embodiment, and thus the irradiation apparatus 400 is balanced irrespective of the rotational positions of the head section in the ψ-direction, as with the third embodiment.

Next, the function of the first balance weight 440 with respect to the rotation in the ψ-direction will be described. Irrespective of the rotational positions of the head section in the ψ-direction, the rotation momentum MPa of the weight of the head section with respect to the X-axis is expressed as $$MPa=Wa \times r1.$$

On the other hand, the rotation momentum MPe of the first balance weight 440 which is connected with the head section through the wire cable 456 and pulleys 458, with respect to the X-axis, is expressed as $$MPe=We \times r2.$$

From E. (2) shown on the third embodiment, We=Wa×r1/r2, we have $$MPa=MPe.$$

The rotation momentum MPe acts to the head section at the position A3 in the opposite direction to the direction in which the head section tends to free-fall, so that the balance for the rotation in the ψ-direction can be maintained irrespective of the rotational positions of the head section in the ψ-direction.

Thus, according to the irradiation apparatus 400 of the fourth embodiment, irrespective of the rotational positions of the head section in the ψ-direction, the balances for the rotation in the Φ-direction and the rotation in the ψ-direction of the weight of the head section and the weight of the balance weight section will be established, and thus only small capacities are required for the motors 122 and 134 and the gear trains 124 and 136 to drive the head section for rotations in the Φ- and ψ-directions so that they may be of relatively light weight. Further, since the first balance weight 440 moves in the opposite direction to that of the head support 114 with respect to the rotation in the ψ-direction, any interference between the first balance weight 440 and the bed B for a patient can be avoided.

Figure 10:
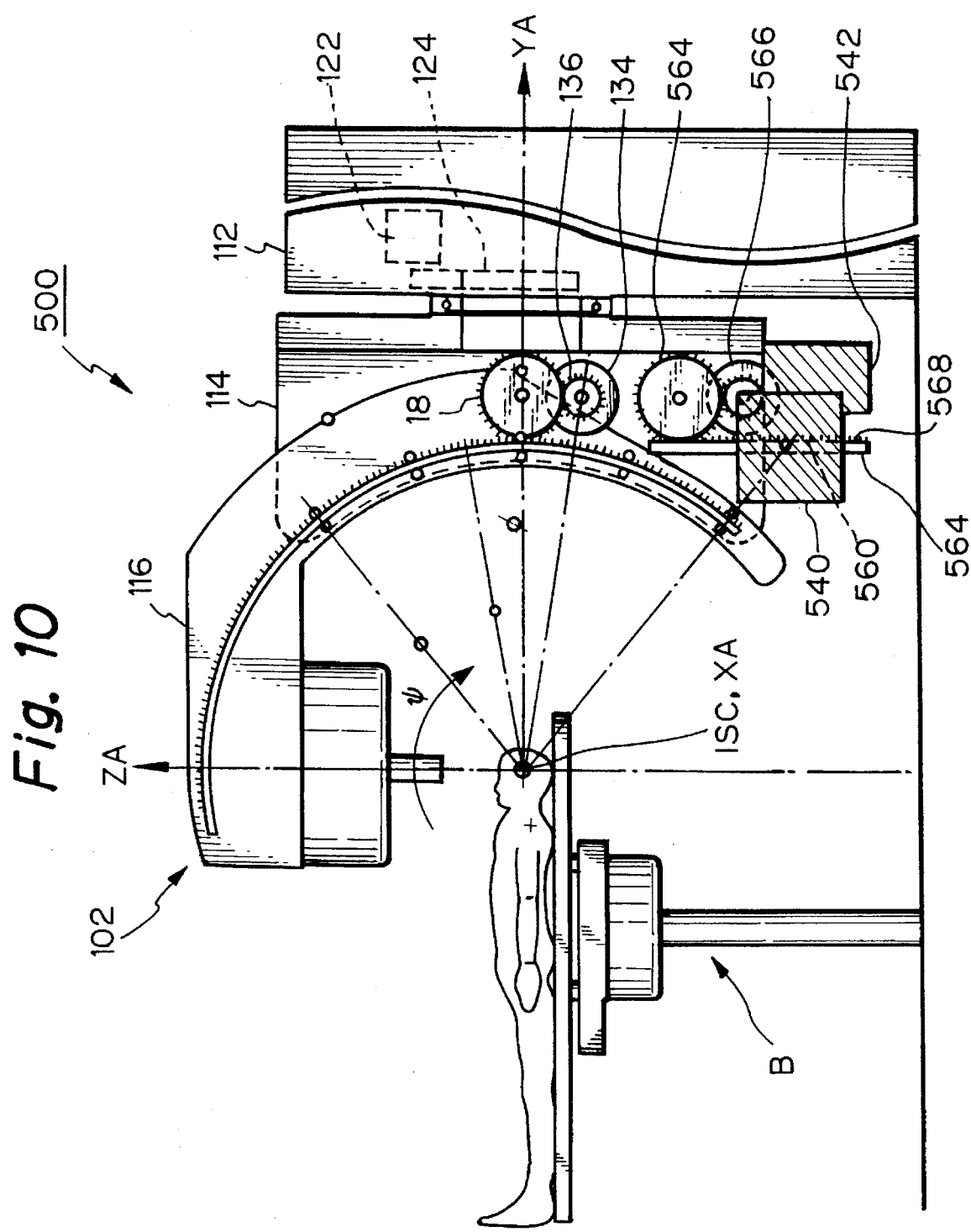
FIG. 10 is a schematic side view of an irradiation apparatus in accordance with a fifth embodiment of the present invention.
Figure 11:
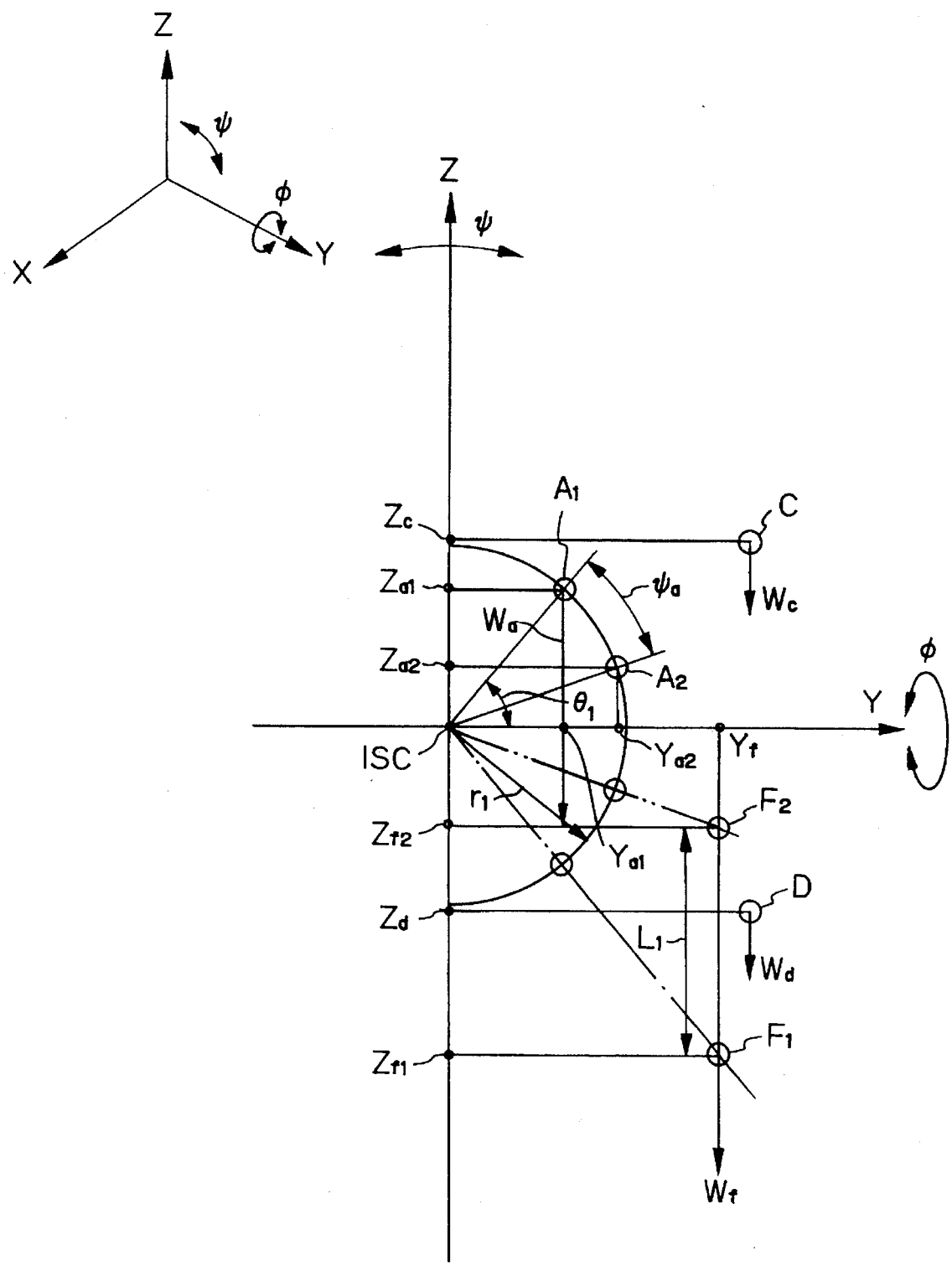
FIG. 11 illustrates the principle of the operation of the irradiation apparatus of FIG. 10.

FIGS. 10 and 11 show an irradiation apparatus 500 according to a fifth embodiment of the present invention. The irradiation apparatus 500 has a balancing mechanism comprising a first balance weight 540 and a second balance weight 542. The second balance weight 542 is fixedly mounted on the rotary support 114 and has the same function and effect as the second balance weight 262 of the second embodiment, that is, it serves to make the rotary support 114 balanced. The first weight 540 is attached to a balance weight support 560 which is supported on the rotary support 114 for linear motion toward and away from the Y-axis YA, in parallel to Z-axis ZA, via a second guide structure (not shown) which may be, for example, any known type of linear slide bearing.

The balance weight support 560 is provided with a third drive mechanism 562 for displacing the balance weight support 560 in relation to the position of the head support 116 relative to the rotary support 114. The third drive mechanism 562 comprises an electric motor 564 mounted on the rotary support 114 and a suitable gear train 566 drivingly connecting the output shaft of the motor 564 to the balance weight support 560, the gear train 566 including a linear rack 568 fixedly mounted on the balance weight support 560 and extending in parallel to Z-axis ZA.

The third drive mechanism 562 displaces the balance weight support 560, under the control of a suitable controller, such that the center of gravity of the combination of the balance weight support 560 and the first balance weight 540 (this combination is referred to as "balance weight section" hereinafter) should be kept lying on a line passing through a) the isocenter ISC and b) the position which is symmetrical to the position of the center of gravity of the head section with respect to the Y-axis.

Referring now to FIG. 11, the operation will be described. In FIG. 11, the designations Wa, Wc, Wd, ψa, A1, A2, C, D, θ1, Ya1, Ya2, Za1, Za2, Zc and Zd represent the same things as they do in connection with the second embodiment, as shown in FIG. 4. Additionally, Wf represents the weight of the balance weight section, F1 represents the initial position of the center of gravity of the balance weight section, and F2 represents the position of the center of gravity of the balance weight section when it has been moved by a linear displacement of L1. Yf is the common Y-coordinate of F1 and F2, Zf1 is the Z-coordinate of F1, and Zf2 is the Z-coordinate of F2.

Suppose that the center of gravity (weighing Wa) of the head section (comprising the head support 116 and the irradiation head 102) is rotated from the initial position A1 (at the initial angle θ1), with the radius r1, by the rotational displacement ψa, into the position A2. During this rotation, the center of gravity (weighing Wf) of the balance weight section (comprising the balance weight support 560 and the first balance weight 540) is moved up along a straight line, from the initial position F1, by the linear displacement L1, into the position F2, while the center of gravity of the balance weight section is kept lying on the line passing through a) the isocenter ISC and b) the position which is symmetrical to the position of the center of gravity of the head section with respect to the Y-axis, as previous mentioned. The rotation balance in this motion will be described hereinafter.

The rotation momentum Ma1 of the weight Wa of the head section effecting on the Y-axis YA when the head section rotates in the Φ-direction is the product of the weight Wa of the head section and Z-coordinate Za1 of the initial position A1 of the head section and thus expressed as $$Ma1 = Wa \times Za1.$$

Similarly, the rotation momentum Mf1 of the weight Wf of the balance weight section effecting on the Y-axis YA when the balance weight section is at the position F1 is expressed as $$Mf1 = Wf \times Zf1.$$

By selecting the weight Wf of the balance weight section as $$Wf = Wa \times Ya1/Yf, \quad (3)$$

we have $$Mf1 = Wa \times Ya1/Yf \times Zf1.$$

The initial position F1 of the center of gravity of the balance weight section is symmetrical to the initial position A1 of the center of gravity of the head section, resulting in $$Zf1 = Yf1 \times \tan\theta 1 = Yf1 \times Za1/Ya1.$$

As shown above, $$Mf1 = Wa \times Za1$$

then $$Ma1 = Mf1$$

meaning that the balance for the rotation in the Φ-direction will be achieved. This relation is satisfied not only when the center of gravity of the head section is at its initial position A1 (at θ1) but also at any positions as long as the center of gravity of the balance weight section is moved while being kept lying on the line passing through a) the isocenter ISC and b) the position which is symmetrical to the position of the center of gravity of the head section with respect to the Y-axis.

Thus, according to the irradiation apparatus 500 of the fifth embodiment, irrespective of the rotational positions of the head section, the balance for the rotation in the Φ-direction of the weight of the head section and the weight of the balance weight section will be established, and further, the balance for the rotation of the rotary support 114 can be achieved in the same manner as the second embodiment. Thus, only small capacities are required for the motors 122 and 134 and the gear trains 124 and 136 to drive the head section for rotations in the Φ- and ψ-directions so that they may be of relatively light weight. Further, since the first balance weight 540 moves in the opposite direction to that of the rotational motion of the head support 114 in the ψ-direction, any interference between the first balance weight 540 and the bed B for a patient can be avoided, and the space under the isocenter ISC is available for better manipulation of the apparatus.

FIGS. 12 and 13 show an irradiation apparatus 600 according to a sixth embodiment of the present invention.

Figure 12A:
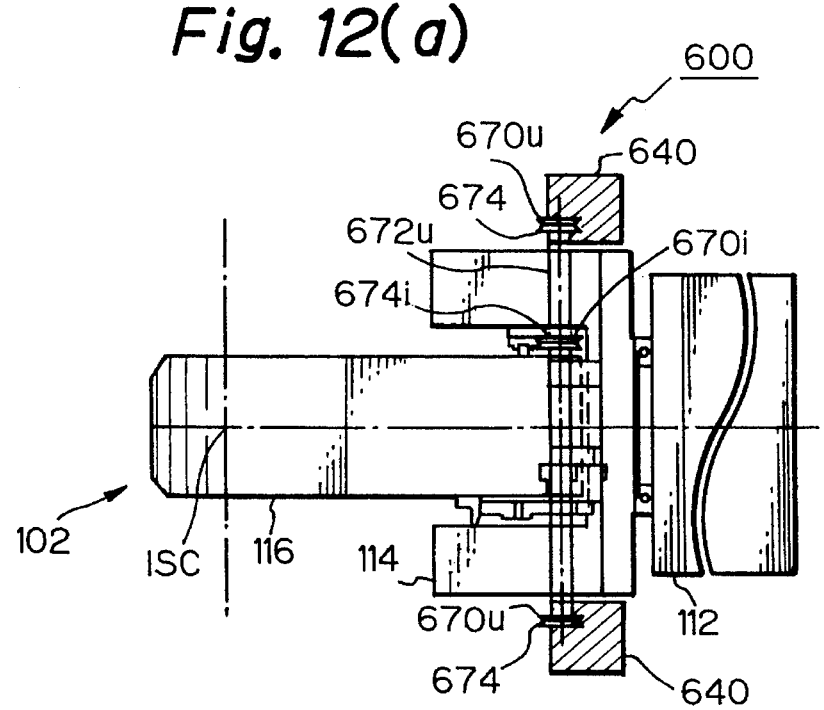
FIG. 12(a) is a top view.
Figure 12B:
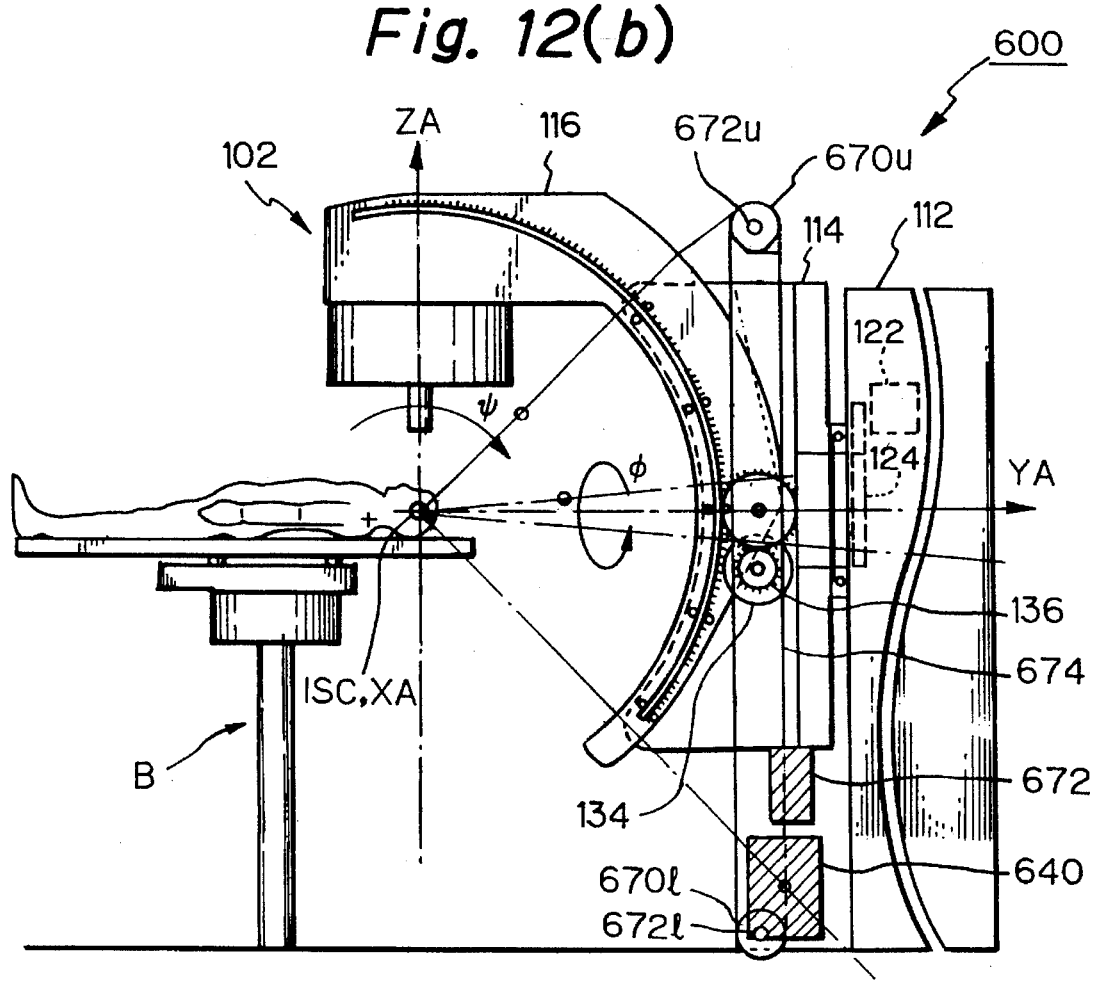
FIG. 12(b) is a side view of an irradiation apparatus in accordance with a sixth embodiment of the present invention.

FIG. 12(a) is a top view, and FIG. 12(b) is a side view of the apparatus 600. FIGS. 13(a) and 13(b) illustrate the principle of the operation of the apparatus 600.

The irradiation apparatus 600 has a balancing mechanism comprising a pair of first balance weights 640 and a second balance weight 642. The second balance weight 642 is fixedly mounted on the rotary support 114 and has the same function and effect as the second balance weight 242 of the second embodiment, that is, it serves to make the rotary support 114 balanced. The first balance weights 640 are supported on the rotary support 114 for linear motion in parallel to Z-axis ZA by means of a suitable linear guide mechanism (not shown). The initial position of the center of gravity of the first balance weights 640 is selected to the position corresponding to the initial position F1 of the center of gravity of the balance weight section of the fifth embodiment. That is, the initial position of the center of gravity of the first balance weights 640 lies on a line passing through a) the isocenter ISC and b) the position which is symmetrical to the position of the center of gravity of the head section with respect to the Y-axis.

The balancing mechanism comprises an interlocking mechanism for keeping the first balance weights 640 and the head support 116 in an interlocking relation with each other. The interlocking mechanism is a wire cable type transmission mechanism comprising a pair of upper pulleys 670u keyed on an upper shaft 672u which is mounted on the upper portion of the rotary support 114 for rotation, a pair of lower pulleys 670l keyed on a lower shaft 672l which is mounted on the lower portion of the rotary support 114 for rotation, and a pair of effectively endless wire cables 674 each trained on one of the upper pulleys 670u and the corresponding one of the lower pulleys 670l and connected to one of the first balance weights 640. The interlocking mechanism further comprises an intermediate pulley 670i keyed on the upper shaft 672u so as to be integrally connected with the upper pulleys 670u, and a connecting wire cable 674i secured to the head support 116 and wound on the intermediate pulley 670i.

In operation, the rotary support 114 is rotated in the Φ-direction by the drive motor 122 through the gear train 124, during which the head section (comprising the head support 116 and the irradiation head 102), the second balance weight 642 and the first balance weights 640 are rotated in the Φ-direction together. In this rotational motion, the balance for the rotation in the Φ-direction among the head section, the rotary support 114, the second balance weight 642 and the first balance weights 640 is maintained as with the fifth embodiment. Further, with respect to the balance for the rotation in the ψ-direction, the tendencies of the head section and the first balance weights 640 to free-fall will counteract each other so that the imbalance for the rotation about the X-axis, and thus the tendency of the irradiation head 102 to free-fall in the rotational direction of ψ may be reduced.

With respect to the rotation of the head section in the ψ-direction, the head support 116 is rotated in this direction by the drive motor 134 through the gear train 136. During this rotation of the head support 116, the connecting wire cable 674i secured to the head support 116 rotates the intermediate pulley 670i, which in turn rotates the upper pulleys 670u on the common upper shaft 672u so as to move, through the wire cables 674, the first balance weights 640 up or down depending on the rotational direction of the head support 116. Specifically, the first balance weights 640 move relative to the Y-axis YA in the opposite direction to that of the head section, thereby reducing the imbalance for the rotation in the Φ-direction. Further, the weight of the first balance weights 640 always acts in the opposite direction to that of the tendency of the irradiation head 102 to free-fall in the rotational direction of ψ, so that the imbalance for the rotation in the ψ-direction can be reduced as well.

Referring now to FIGS. 13(a) and 13(b), the balance relationship between the components involved in the above operation will be described. In FIGS. 13(a) and 13(b), the designations Wa, Wc, Wd, Wf, ψa, θ1, A1, A2, C, D1, F1, F2, Ya1, Ya2, Za1, Za2, Zc, Zd, Zf1 and Zf2 represent the same things as they do in connection with the fifth embodiment, as shown in FIG. 11. Additionally, H1 represents the point fixed relative to the head support 166, which lies on a line passing through the isocenter ISC and the position A1 and has its Y-coordinate equal to Yh. H2 represents the position into which the point H1 is moved when the center of gravity of the head section moves from the initial position A1 into the position A2. 670u and 670i represent the upper and intermediate pulleys, respectively. 674 and 674i represent the cable wires. Wh the free-fall weight at the point H1.

With respect to the balance for the rotation in the Φ-direction, motions of the head section and the first balance weights 640 are the same with those i the fifth embodiment, and the balance is established at any rotational position in the ψ-direction of the head section as shown in connection with the fifth embodiment.

Next, the balance for the rotation about X-axis will be described. The free-fall load Wa1 of the head section in the rotational direction of Φ, caused by the weight Wa of the head section when its center of gravity is at the position A1, is shown in FIG. 13(b) and expressed as $$Wa1 = Wa\cos\theta1.$$

The vertical free-fall load Wa2 of the load Wa1 is expressed as $$Wa2 = Wa1\cos\theta1 = Wa\cos^2\theta1.$$

Therefore, the vertical free-fall load Wh of the head section at the point H1 is expressed as $$Wh = (Ya1/Yf)\,Wa2 = (Ya1/Yf)\,Wa\times\cos^2\theta1.$$

At the point H1, the weight Wf of the first balance weights 640 always acts upwardly in a constant magnitude, so that the balance at the point H1 is, from the E. (3) shown in conjunction with the fifth embodiment, expressed by the following equation.

$$Wf - Wh = Wa\times Ya1/Yf - Wa2\times Ya1/Yf,$$

thus $$Wf - Wh = Wa\times Ya1/Yf - Wa\times(Ya1/Yf)\times\cos^2\theta1 = Wa\times(Ya1/Yf)\times(1-\cos^2\theta1),$$

meaning that the imbalance is highly reduced. The imbalance will be maximized when $\cos\theta1=1$, and thus $\theta1=0$.

Thus, according to the irradiation apparatus 600 of the sixth embodiment, by virtue of the function of the first movable balance weights 640, both the imbalances for the rotation in the Φ-direction and the rotation in the ψ-direction can be reduced. Thereby the tendency of the head section to free-fall in the rotational direction of ψ is reduced, and only small capacities are required for the motors 122 and 134 and the gear trains 124 and 136 to drive the head section for rotations in the Φ- and ψ-directions so that they may be of relatively light weight. Further, since the first balance weights 640 move along paths which are remote from the isocenter ISC, any interference between the first balance weights 640 and the bed B for a patient can be avoided irrespective of the rotational positions of the head support 116 about the X-axis, and the space under the isocenter ISC is available for better manipulation of the apparatus.

Figure 14A:
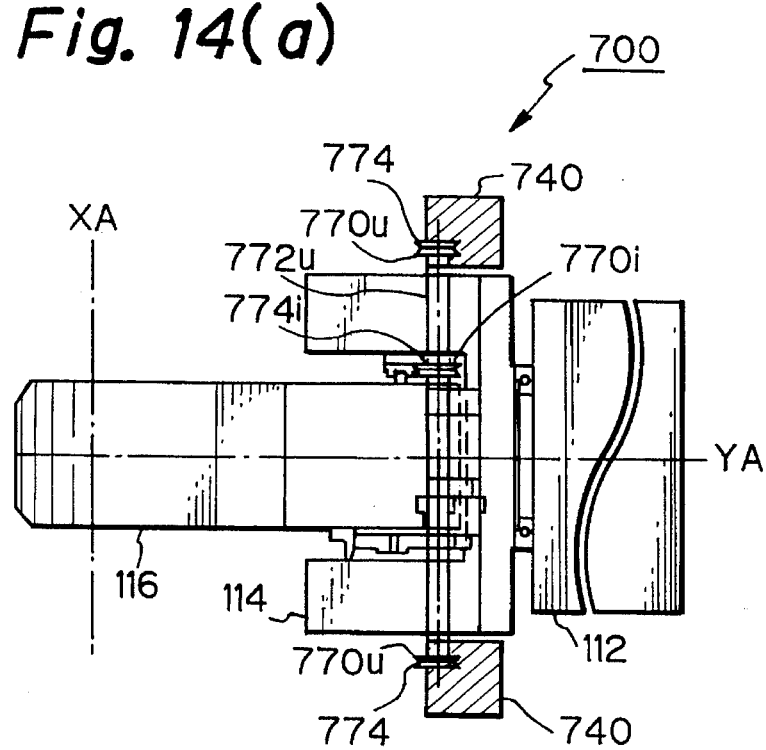
FIG. 14(a) is a top view.
Figure 14B:
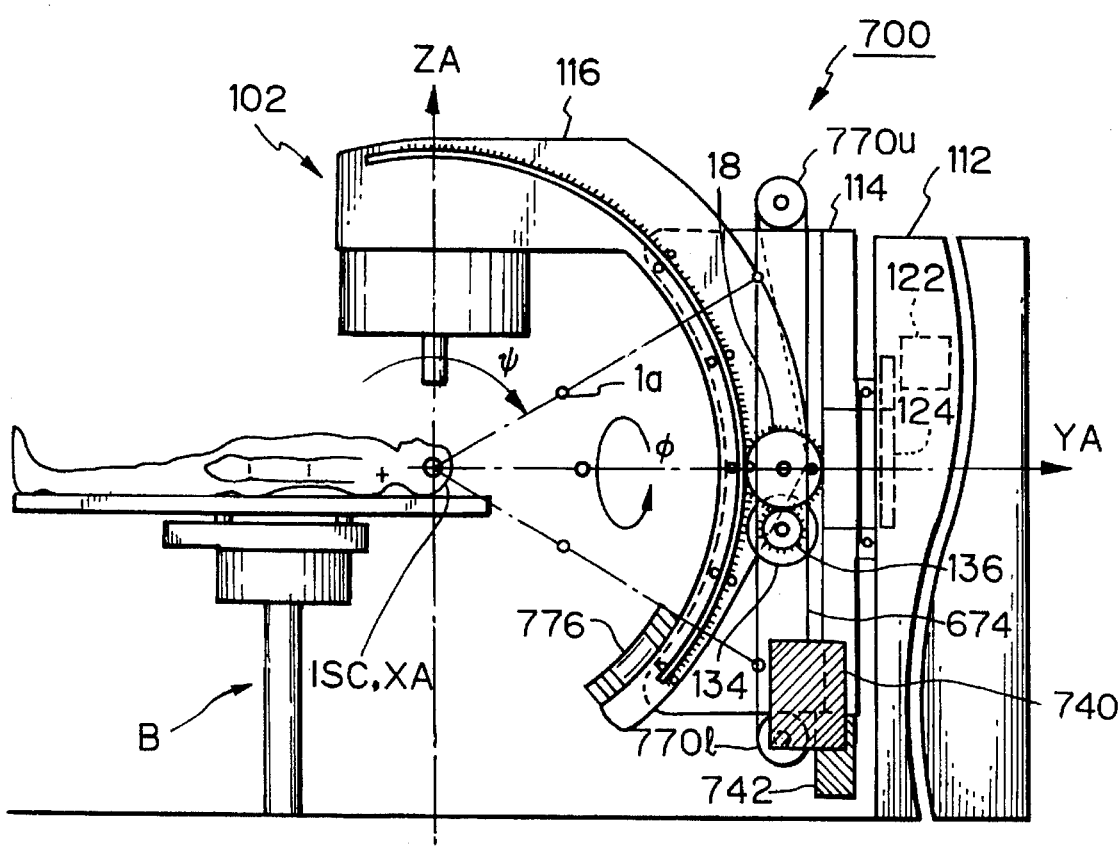
FIG. 14(b) is a side view of an irradiation apparatus in accordance with a seventh embodiment of the present invention.
Figure 15:
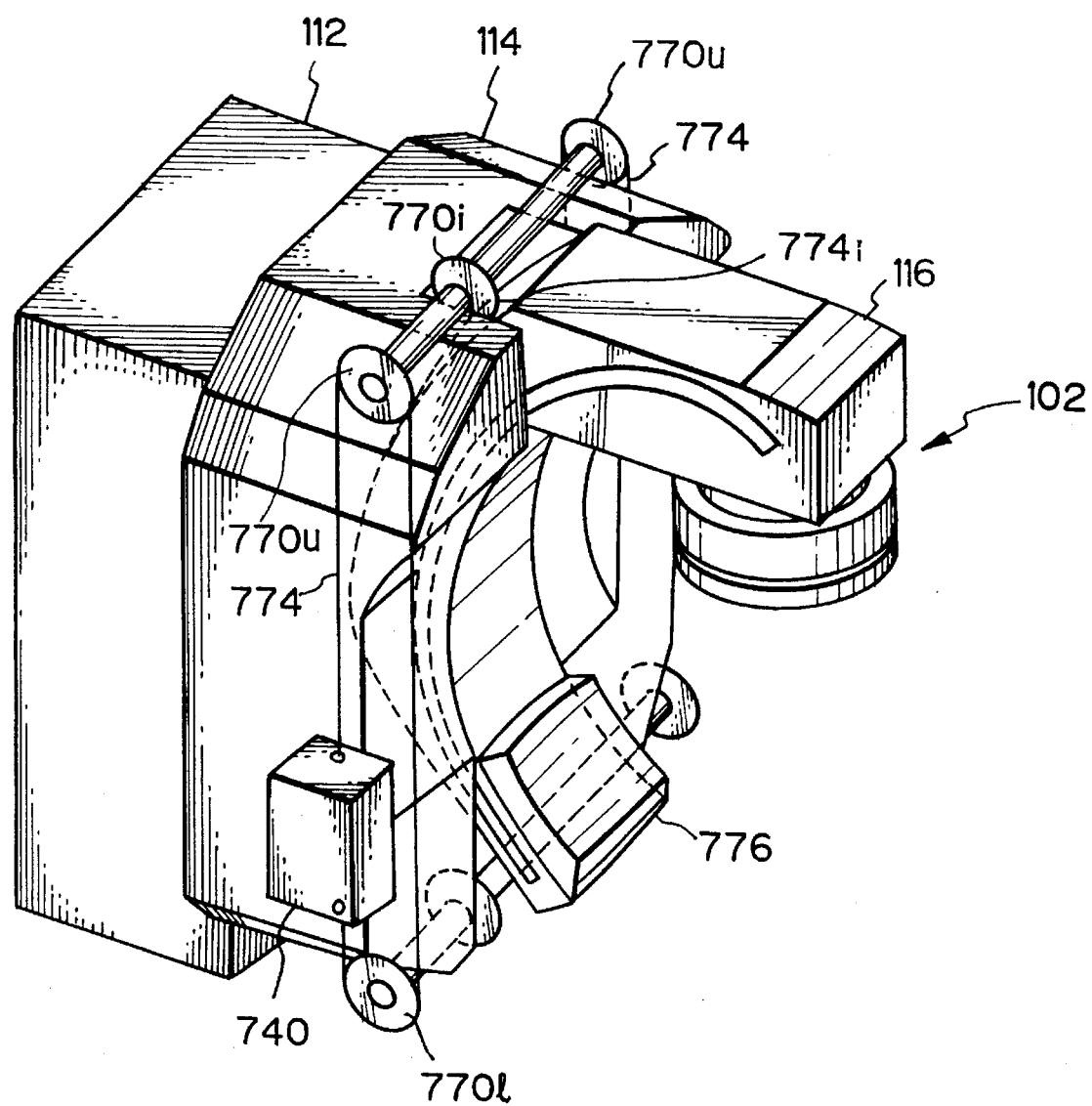
FIG. 15 is an isometric view of the interlocking mechanism used in the irradiation apparatus of FIGS. 14(a) and 14(b)

FIGS. 14 and 15 show an irradiation apparatus 700 according to a seventh embodiment of the present invention. FIG. 14(*a*) is a top view, and FIG. 14(*b*) is a side view of the apparatus 700. FIG. 15 is an isometric view of the interlocking mechanism used in the apparatus 700.

The irradiation apparatus 700 has a balancing mechanism comprising a pair of first balance weights 740, a second balance weight 742 and a third balance weight 776. The second balance weight 742 is fixedly mounted on the rotary support 114 and has the same function and effect as the second balance weight 242 of the second embodiment, that is, it serves to make the rotary support 114 balanced. The first balance weights 740 are supported on the rotary support 114 for linear motion in the same manner as the first balance weights 640 of the sixth embodiment. The balancing mechanism comprises an interlocking mechanism which is the same in function with that used in the sixth embodiment. Corresponding components of these interlocking mechanisms are designated by the same reference numerals with the first digit thereof changed from 6 to 7 for the interlocking mechanism of the seventh embodiment.

The third balance weight 776 is fixedly mounted on the lower portion of the head support 116 and has its weight and position selected such that the center of gravity of the combination of the head support 116, the irradiation head 102 and the third balance weight 776 (this combination is referred to as "head section" with respect to this and the following embodiments) lies on the Y-axis YA when the center of gravity of the head section has been rotated in the ψ-direction by a certain rotational displacement.

In operation, the rotary support 114 is rotated in the Φ-direction by the drive motor 122 through the gear train 124, during which the head section (including the third balance weight 776), the second balance weight 742 and the first balance weights 740 are rotated in the Φ-direction together. In this rotational motion, the balances for the rotation in the Φ-direction of the head section, the rotary support 114, the second balance weight 742 and the first balance weights 740 is maintained as with the fifth embodiment. Further, with respect to the balance for the rotation in the ψ-direction, the load produced by the weight of the head section and the ψ-direction rotation free-fall force produced by the first balance weights 740 will counteract each other so that the imbalance for the rotation about the X-axis, and thus the tendency of the irradiation head 102 to free-fall in the rotational direction of ψ may be reduced.

With respect to the rotation of the head section in the ψ-direction, the head support 116 is rotated in this direction by the drive motor 134 through the gear train 136. During this rotation of the head support 116, the connecting wire cable 774*i* secured to the head support 116 rotates the intermediate pulley 770*i*, which in turn rotates the upper pulleys 770*u* on the common upper shaft 772*u* so as to move, through the wire cables 774, the first balance weights 740 up or down depending on the rotational direction of the head support 116. Specifically, the first balance weights 740 are moved in the opposite direction to the moving direction of the center of gravity of the head section with respect to the Y-axis YA, thereby reducing the imbalance for the rotation in the Φ-direction. Further, the weight of the first balance weights 740 always acts in the opposite direction to the direction of the tendency of the head section to free-fall so as to rotate about the X-axis, so that the imbalance for the rotation in the ψ-direction can be reduced as well.

As shown in the description of the sixth embodiment above, the balance relationship established by the interlocking mechanism which is used in both the sixth and this seventh embodiments depends on and varies with the value of $(1-\cos^2\theta 1)$. In this embodiment, by virtue of the provision of the third balance weight 776, the value of $(1\cos^2\theta 1)$, and thus the imbalance of the components, may be further reduced over the sixth embodiment.

Specifically, since the center of gravity of the head section (comprising the head support 116, the irradiation head 102 and the third balance weight 776) is rotated in the ψ-direction symmetrically with respect to the Y-axis, the variation in the ψ-direction rotation free-fall load may be minimized, and thus the imbalance for the rotation in the ψ-direction may be further reduced over the sixth embodiment. In addition, since the initial position of the first balance weights 740 may be set at a relatively high level, the isocenter ISC may be positioned at a relatively low level, so that the irradiation apparatus may be formed in a more compact configuration.

Thus, according to the irradiation apparatus 700 of the seventh embodiment, by virtue of the functions of the first movable balance weights 740 and the third balance weight 776, both the imbalances for the rotation in the Φ-direction and the rotation in the ψ-direction may be reduced. Thereby the tendency of the head section to free-fall in the rotational direction of ψ is reduced, and only small capacities are required for the motors 122 and 134 and the gear trains 124 and 136 to drive the head section for rotations in the Φ- and ψ-directions so that they may be of relatively light weight. Further, since the first balance weights 740 move along paths which are remote from the isocenter ISC, any interference of the first balance weights 740 with the bed B for a patient can be avoided, and the space under the isocenter ISC is available for better manipulation of the apparatus. In addition, by virtue of the provision of the third balance weight 776, the initial position of the first balance weights 740 may be set at a relatively high level, and thus the isocenter ISC may be lowered, so that the manipulability of the apparatus may be further enhanced and the irradiation apparatus may be formed in a more compact configuration.

Figure 16A:
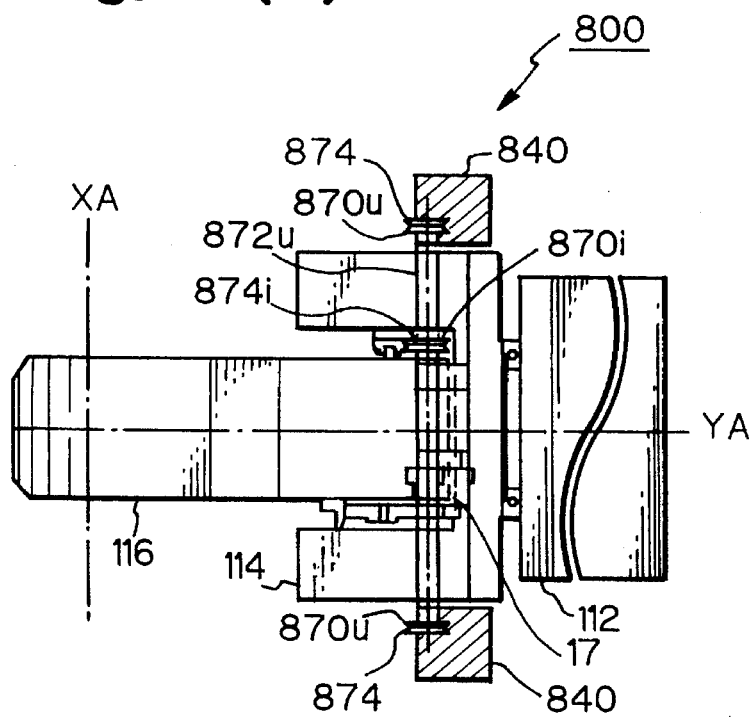
FIG. 16(a) is a top view.
Figure 16B:
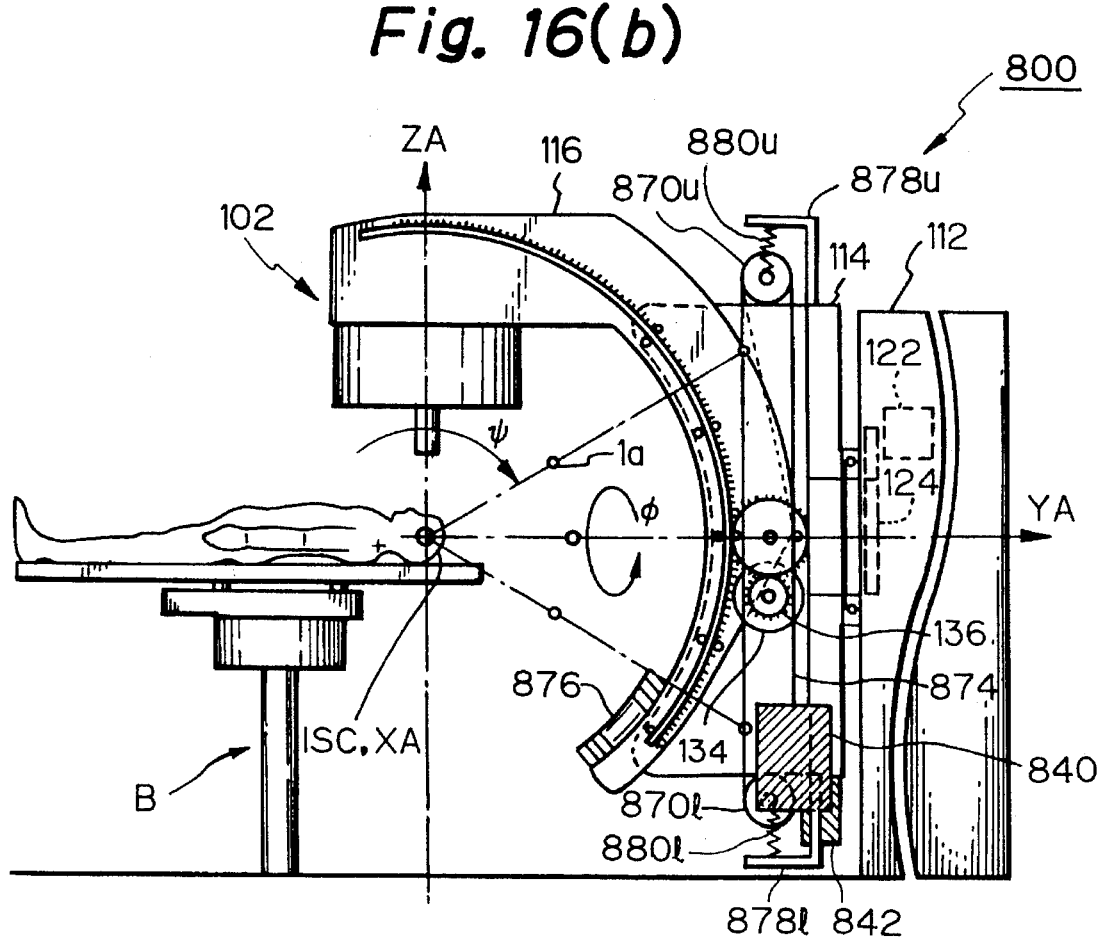
FIG. 16(b) is a side view of an irradiation apparatus in accordance with an eighth embodiment of the present invention.

FIGS. 16 and 17 show an irradiation apparatus 800 according to an eighth embodiment of the present invention. FIG. 16(*a*) is a top view, and FIG. 16(*b*) is a side view of the apparatus 800. FIG. 17 is an isometric view of the interlocking mechanism used in the apparatus 800.

The irradiation apparatus 800 has a balancing mechanism comprising a pair of first balance weights 840, a second balance weight 842 and a third balance weight 876. The balancing mechanism further comprises an interlocking mechanism for keeping the first balance weights 840 and the head support 116 in an interlocking relation with each other.

The irradiation apparatus 800 of the eighth embodiment uses the same balancing mechanism and the same interlocking mechanism as the irradiation apparatus 700 of the seventh embodiment except that a tension mechanism is incorporated into the interlocking mechanism of the eighth embodiment. Corresponding components of the interlocking mechanisms of the seventh and eighth embodiments are designated by the same reference numerals with the first digit thereof changed from 7 to 8 for the interlocking mechanism of the eighth embodiment.

The tension mechanism comprises an upper and lower brackets 878*u* and 878*l* fixedly mounted on the upper and lower ends of the rotary support 114, respectively, a set of upper tension units 880*u* attached to the upper bracket 878*u* for pulling up the upper and intermediate pulleys 870*u* and 870*i*, and a set of lower tension units 880*l* attached to the lower bracket 878*l* for pulling down the lower pulleys 870*l*. The upper and lower tension units 880*u* and 880*l* serves to eliminate any loosening of the wire cables 874 which would otherwise occur due to the greater stroke of the connecting wire cable 874*i* secured to the head support 116 than that of the wire cables 874 connected to the first balance weights 840.

In operation, the rotary support 114 is rotated in the Φ-direction by the drive motor 122 through the gear train 124, during which the head section (comprising the head support 116, irradiation head 102 and the third balance weight 876), the second balance weight 842 and the first balance weights 840 are rotated in the Φ-direction together. In this rotational motion, the balance for the rotation in the Φ-direction of the head section, the rotary support 114, the second balance weight 842 and the first balance weights 840 is maintained as with the fifth embodiment. Further, with respect to the balance for the rotation in the ψ-direction, the load produced by the weight of the head section and the ψ-direction rotation free-fall force produced by the first balance weights 840 will counteract each other so that the imbalance for the rotation in the ψ-direction, and thus the tendency of the irradiation head 102 to free-fall in the rotational direction of ψ may be reduced.

With respect to the rotation of the head section in the ψ-direction, the head support 116 is rotated in this direction by the drive motor 134 through the gear train 136. During this rotation of the head support 116, the connecting wire cable 874*i* secured to the head support 116 rotates the intermediate pulley 870*i*, which in turn rotates the upper pulleys 870*u* on the common upper shaft 872*u* so as to move, through the wire cables 874, the first balance weights 840 up or down depending on the rotational direction of the head support 116. Specifically, the first balance weights 840 are moved in the opposite direction to the moving direction of the center of gravity of the head section with respect to the Y-axis YA, thereby reducing the imbalance for the rotation in the Φ-direction. Further, the weight of the first balance weights 840 always acts in the opposite direction to the direction of the tendency of the head section to free-fall so as to rotate about the X-axis, so that the imbalance for the rotation in the ψ-direction can be reduced as well.

In this motion of the components, the securing point of the connecting wire cable 874*i* to the head support 116 moves along an arcuate path following the rotational motion of the head section in the ψ-direction, while the wire cables 874 connected with the first balance weights 840 move along linear paths following the motion of the latter, so that there is a difference between the strokes of the connecting wire cable 874*i* and the other two wire cables 874. While this tends to cause the wire cables 874 to loosen, any such loosening can be effectively eliminated by the tension units 880*u* and 880*l* which always serve to impose a tension onto each of the wire cables 874.

Thus, according to the irradiation apparatus 800 of the eighth embodiment, by virtue of the functions of the first movable balance weights 840 and the third balance weight 876, both the imbalances for the rotation in the Φ-direction and the rotation in the ψ-direction may be reduced. Thereby the tendency of the head section to free-fall in the rotational direction of ψ is reduced, and only small capacities are required for the motors 122 and 134 and the gear trains 124 and 136 to drive the head section for rotations in the Φ- and ψ-directions so that they may be of relatively light weight.

By virtue of the function of the tension mechanism, any loosening of the wire cables 874 can be eliminated, so that any error in the positioning of the first balance weights 840, which could increase the imbalance, may be minimized. Further, since the first balance weights 840 move along paths which are remote from the isocenter ISC, any interference of the first balance weights 840 with the bed B for a patient can be avoided, and the space under the isocenter ISC is available for better manipulation of the apparatus. In addition, by virtue of the provision of the third balance weight 876, the initial position of the first balance weights 840 may be set at a relatively high level, and thus the isocenter ISC may be lowered, so that the manipulability of the apparatus may be further enhanced and the irradiation apparatus may be formed in a more compact configuration.

Figure 18A:
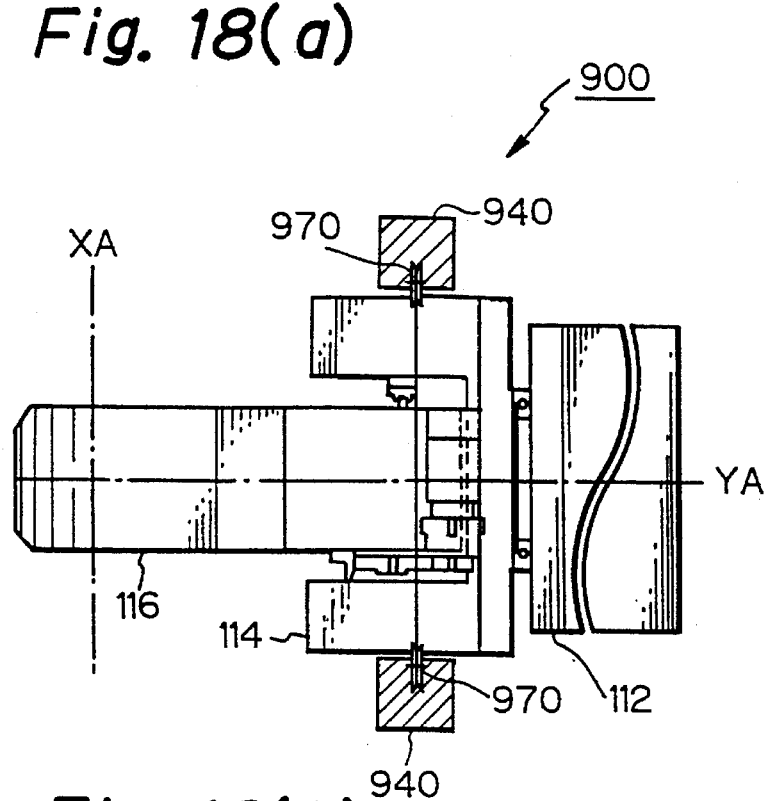
FIG. 18(a) is a top view.
Figure 18B:
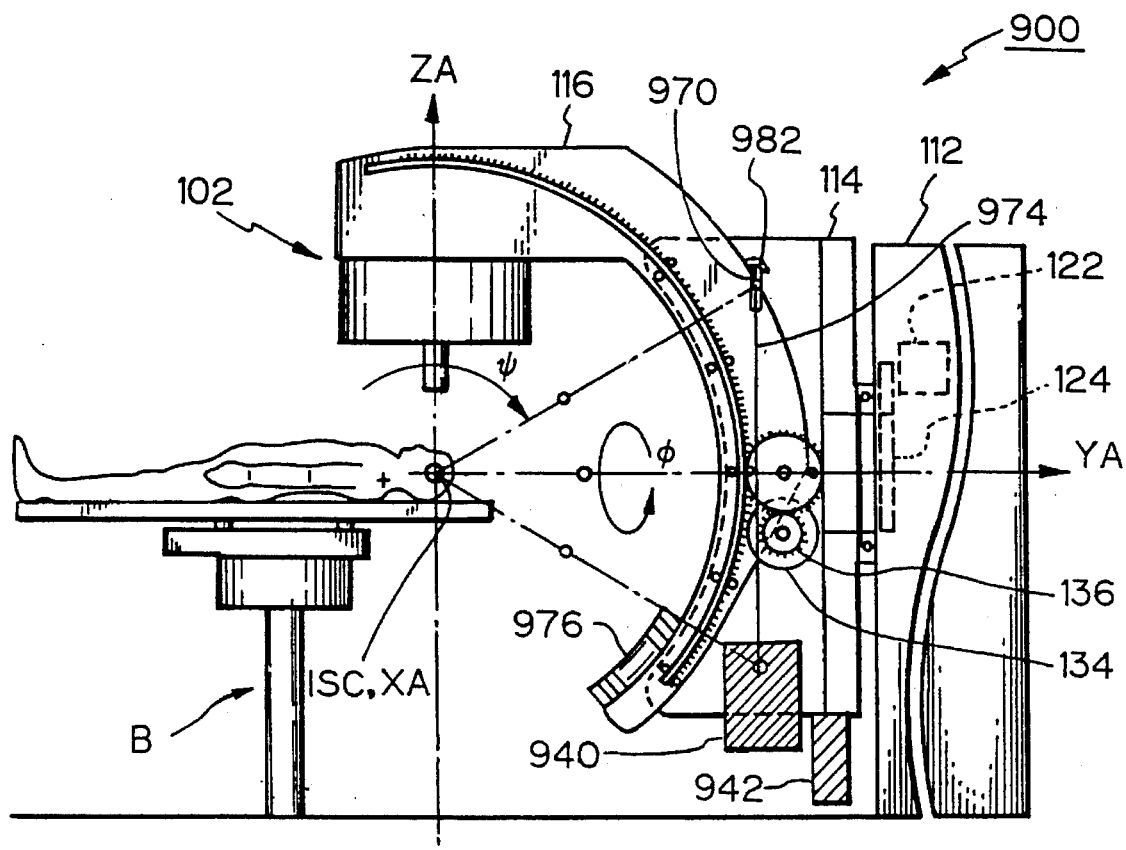
FIG. 18(b) is a side view of an irradiation apparatus in accordance with a ninth embodiment of the present invention.
Figure 19:
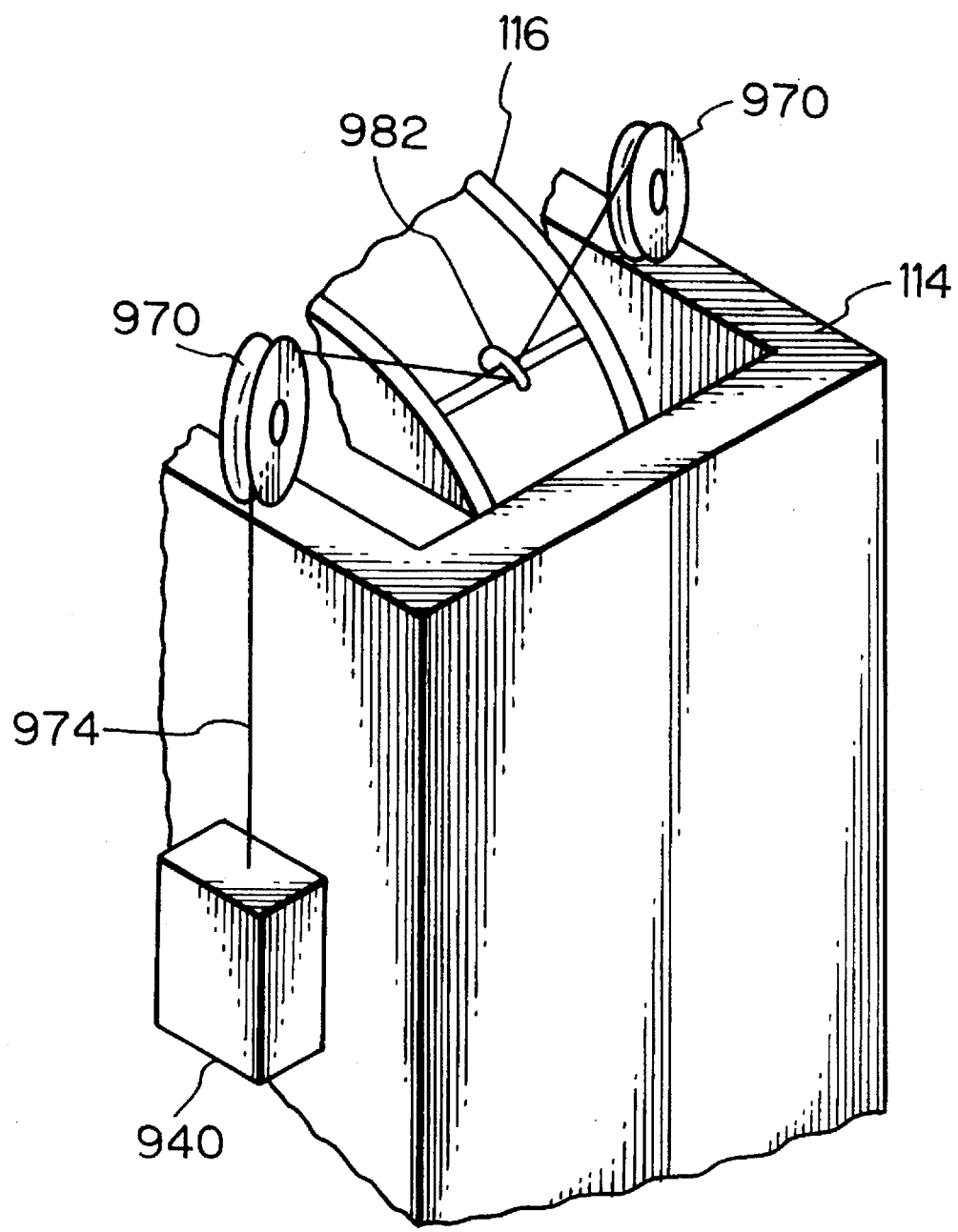
FIG. 19 is an isometric view of the interlocking mechanism used in the irradiation apparatus of FIGS. 18(a) and 18(b)

FIGS. 18 and 19 show an irradiation apparatus 900 according to a ninth embodiment of the present invention. FIG. 18(*a*) is a top view, and FIG. 18(*b*) is a side view of the apparatus 900. FIG. 19 is an isometric view of the interlocking mechanism used in the apparatus 900.

The irradiation apparatus 900 has a balancing mechanism comprising a pair of first balance weights 940, a second balance weight 942 and a third balance weight 976. The balancing mechanism further comprises an interlocking mechanism for keeping the first balance weights 940 and the head support 116 in an interlocking relation with each other.

The irradiation apparatus 900 of the ninth embodiment uses the same balancing mechanism as the irradiation apparatus 700 of the seventh embodiment except that the interlocking mechanism of the ninth embodiment has a simpler arrangement than that of the seventh embodiment. Corresponding components of the balancing mechanisms of the seventh and ninth embodiments are designated by the same reference numerals with the first digit thereof changed from 7 to 9 for the balancing mechanism of the ninth embodiment.

The interlocking mechanism is a wire cable type transmission mechanism comprising a pair of pulleys 970 mounted on the upper portion of the rotary support 114 for rotation, a fixture 984 fixedly attached to the head support 116 and a pair of connecting wire cables 974 each connected at one end to the fixture 984, trained on and guided by the corresponding one of the pulleys 970 and connected at the other end to the corresponding one of the first balance weights 940.

In operation, the rotary support 114 is rotated in the Φ-direction by the drive motor 122 through the gear train 124, during which the head section (comprising the head support 116, irradiation head 102 and the third balance weight 976), the second balance weight 942 and the first balance weights 940 are rotated in the Φ-direction together. In this rotational motion, the balance for the rotation in the Φ-direction of the head section, the rotary support 114, the second balance weight 942 and the first balance weights 940 is maintained as with the fifth embodiment. Further, with respect to the balance for the rotation in the ψ-direction, the load produced by the weight of the head section and the ψ-direction rotation free-fall force produced by the first balance weights 940 will counteract each other so that the imbalance for the rotation in the ψ-direction, and thus the tendency of the irradiation head 102 to free-fall in the rotational direction of ψ may be reduced.

With respect to the rotation of the head section in the ψ-direction, the head support 116 is rotated in this direction by the drive motor 134 through the gear train 136. During this rotation of the head support 116, the fixture 982 fixedly attached to the head support 116 pulls down the associated ends of the connecting wire cables 974 so as to move the first balance weights 940 in the opposite direction to the moving direction of the center of gravity of the head section with respect to the Y-axis YA, thereby reducing the imbalance for the rotation in the Φ-direction. Further, the weight of the first balance weights 940 always acts in the opposite direction to the direction of the tendency of the head section to free-fall so as to rotate about the X-axis, so that the imbalance for the rotation in the ψ-direction can be reduced as well. In addition, since the interlocking mechanism uses only the connecting wire cables 974 and the fixture 982 in order to transmit the force between the head section and the first balance weights 940, there is provided a simple arrangement for converting a rotational motion into a liner motion.

Thus, according to the irradiation apparatus 900 of the ninth embodiment, by virtue of the functions of the first movable balance weights 940 and the third balance weight 976, both the imbalances for the rotation in the Φ-direction and the rotation in the ψ-direction may be reduced. Thereby the tendency of the head section to free-fall in the rotational direction of ψ is reduced, and only small capacities are required for the motors 122 and 134 and the gear trains 124 and 136 to drive the head section for rotations in the Φ- and ψ-directions so that they may be of relatively light weight. Since the interlocking mechanism for driving the first balance weights 940 uses the connecting wire cables 974 and the fixture 982, the arrangement of the irradiation apparatus may be made more simple. Further, since the first balance weights 940 move along paths which are remote from the isocenter ISC, any interference of the first balance weights 940 with the bed B for a patient can be avoided, and the space under the isocenter ISC is available for better manipulation of the apparatus. In addition, by virtue of the provision of the third balance weight 976, the initial position of the first balance weights 940 may be set at a relatively high level, and thus the isocenter ISC may be lowered, so that the manipulability of the apparatus may be further enhanced and the irradiation apparatus may be formed in a more compact configuration.

Figure 20A:
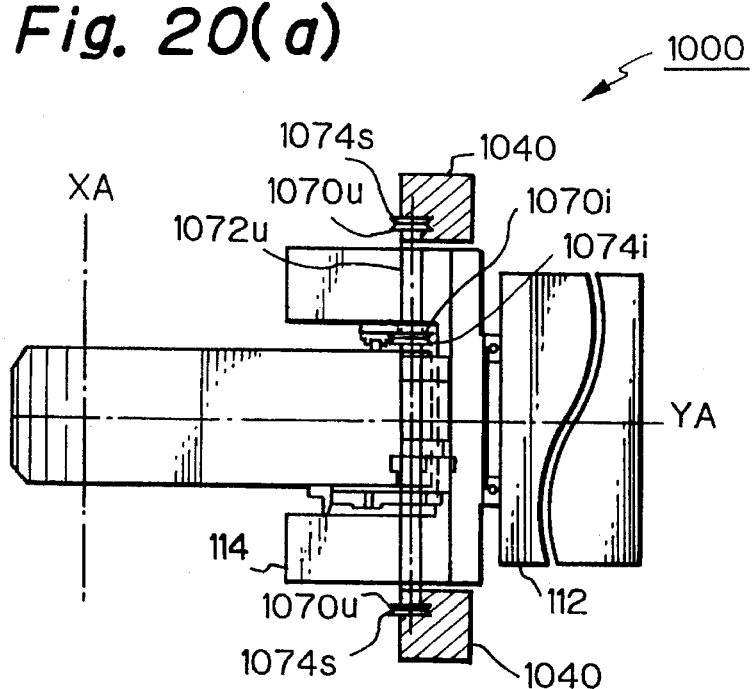
FIG. 20(a) is a top view.
Figure 20B:
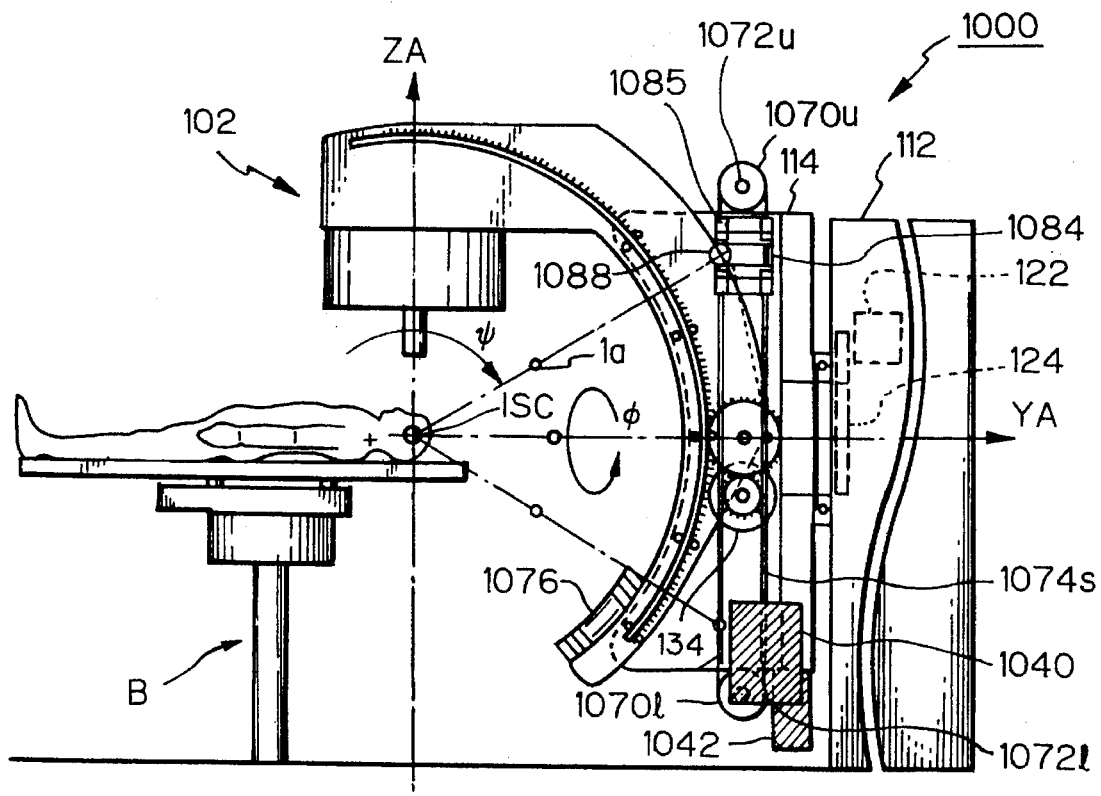
FIG. 20(b) is a side view of an irradiation apparatus in accordance with a tenth embodiment of the present invention.
Figure 21:
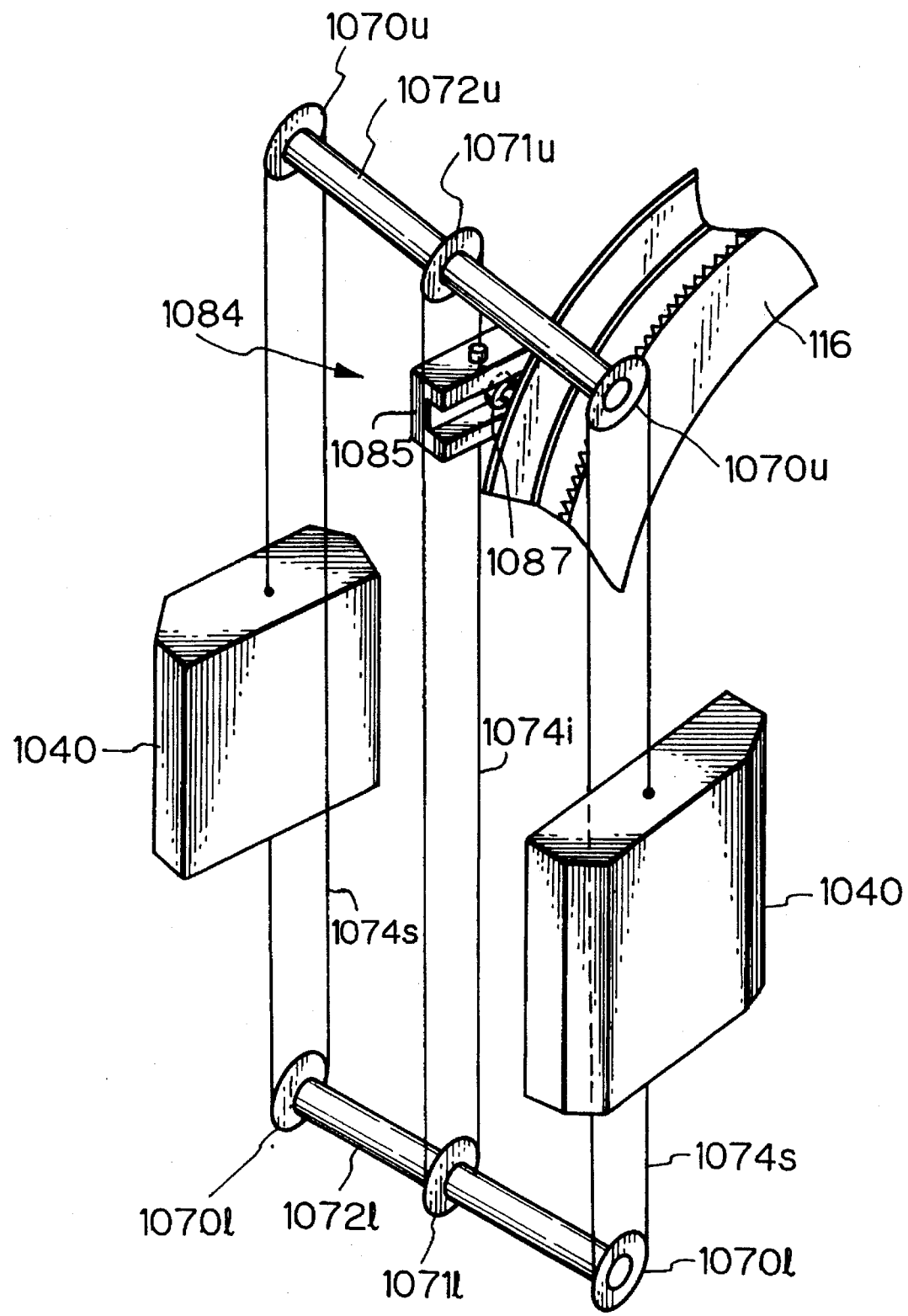
FIG. 21 is an isometric view of the interlocking mechanism used in the irradiation apparatus of FIGS. 20(a) and 20(b)
Figure 22:
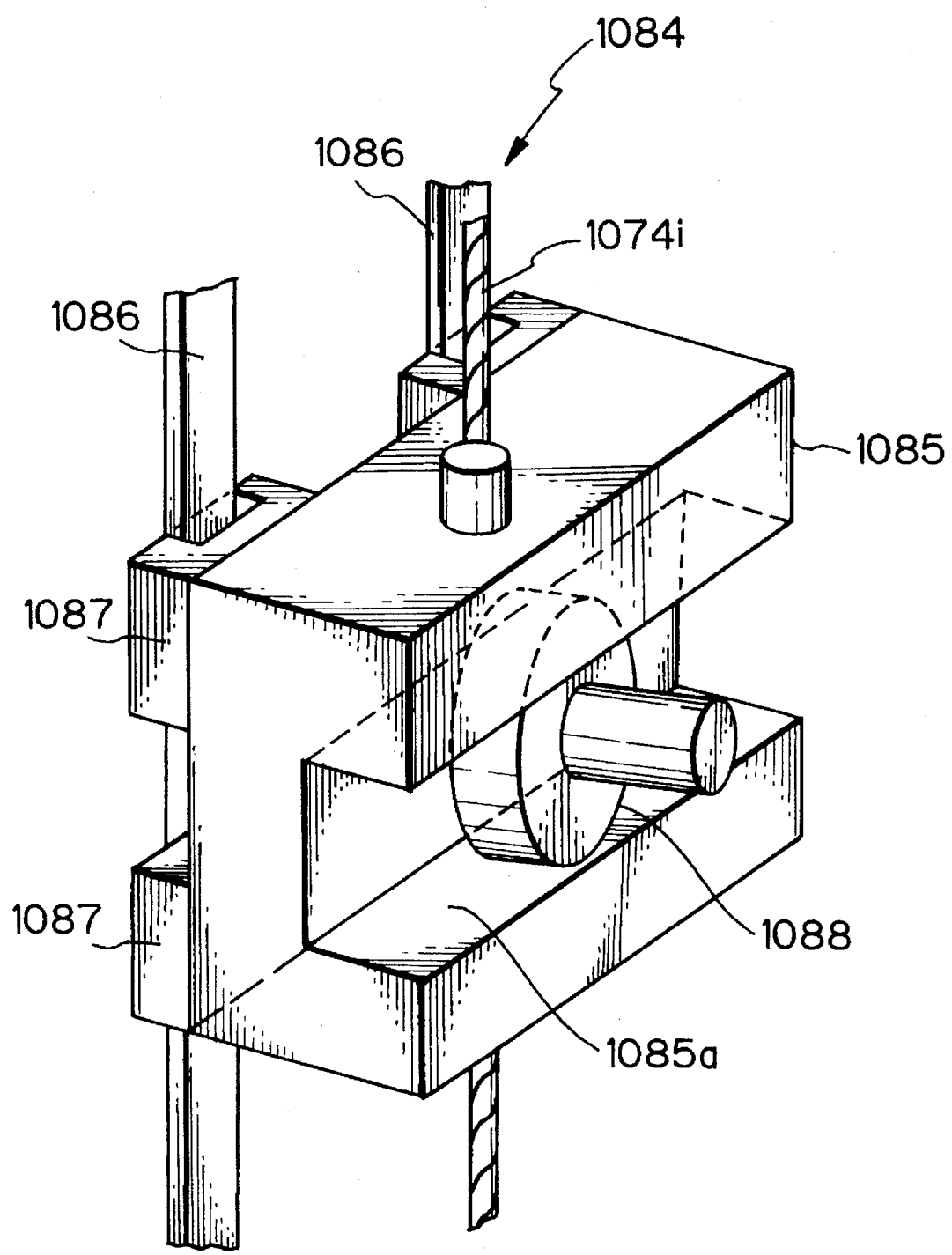
FIG. 22 is an isometric view of the cam mechanism used in the interlocking mechanism of FIG. 21.

FIGS. 20 through 22 show an irradiation apparatus 1000 according to a tenth embodiment of the present invention. FIG. 20(a) is a top view, and FIG. 20(b) is a side view of the apparatus 1000. FIG. 21 is an isometric view of the interlocking mechanism used in the apparatus 1000. FIG. 22 is an isometric view of the cam mechanism used in the interlocking mechanism of FIG. 21.

The irradiation apparatus 1000 has a balancing mechanism comprising a pair of first balance weights 1040, a second balance weight 1042 and a third balance weight 1076. The balancing mechanism further comprises an interlocking mechanism for keeping the first balance weights 1040 and the head support 116 in an interlocking relation with each other.

The irradiation apparatus 1000 of the tenth embodiment uses the same balancing mechanism as the irradiation apparatus 700 of the seventh embodiment except that the interlocking mechanism of the tenth embodiment is different to that of the seventh embodiment.

The interlocking mechanism of the tenth embodiment is a wire cable type transmission mechanism comprising a pair of upper side pulleys 1070u keyed on an upper shaft 1072u which is mounted on the upper portion of the rotary support 114 for rotation, a pair of lower side pulleys 1070l keyed on a lower shaft 1072l which is mounted on the lower portion of the rotary support 114 for rotation, and a pair of effectively endless side wire cables 1074s each trained on one of the upper side pulleys 1070u and the corresponding one of the lower side pulleys 1070l and connected to one of the first balance weights 1040. The interlocking mechanism further comprises an upper intermediate pulley 1071i keyed on the upper shaft 1072u so as to be integrally connected with the upper side pulleys 1070u, a lower intermediate pulley 1071l keyed on the lower shaft 1072l so as to be integrally connected with the lower side pulleys 1070l, an effectively endless intermediate wire cable 1074i trained on the upper and lower intermediate pulleys 1071u and 1071l, and a cam mechanism 1084 operatively connected to the head support 116 (and thus the head section) and intermediate wire cable 1074i for converting the rotational motion of the head section to the linear motion of the intermediate wire cable 1074i. The main portions of the wire cables 1074s and 1074i extend in parallel to the Z-axis ZA.

The cam mechanism 1084 comprises a crosshead 1085 connected with the intermediate wire cable 1074i and guided by a linear guide unit for nonrotatable, linear motion in parallel to the Z-axis ZA. The linear guide unit comprises a pair of straight guide rails 1086 fixed on the rotary support 114 and extending in parallel to the Z-axis and four guide blocks 1087 in sliding engagement with the guide rails 1086 and attached to the crosshead 1085. As clearly shown in FIG. 21, when the intermediate wire cable 1074i circulates on the pulleys 1071u and 1071l, the crosshead 1085 moves in parallel to the Z-axis.

The crosshead 1085 has a guide slot 1085a extending in parallel to the Y-axis YA, and thus perpendicular to the Z-axis ZA. The cam mechanism 1084 further comprises a cam roller 1088 mounted on the head support 116 for rotation about an axis parallel to the X-axis. The cam roller 1088 is in cam-engagement with the guide slot 1085a of the crosshead 1085. When the head support 116 (and thus the head section) is rotated about the X-axis XA, the cam roller 1088 travels along an arcuate path so as to move the crosshead 1085 linearly in parallel to the Z-axis ZA. In this manner, the rotational motion of the head section is converted to a linear motion of the first balance weights 1040.

In operation, the rotary support 114 is rotated in the Φ-direction by the drive motor 122 through the gear train 124, during which the head section (comprising the head support 116, irradiation head 102 and the third balance weight 1076), the second balance weight 1042 and the first balance weights 1040 are rotated in the Φ-direction together. In this rotational motion, the balance for the rotation in the Φ-direction of the head section, the rotary support 114, the second balance weight 1042 and the first balance weights 1040 is maintained as with the fifth embodiment. Further, with respect to the balance for the rotation in the ψ-direction, the load produced by the weight of the head section and the ψ-direction rotation free-fall force produced by the first balance weights 1040 will counteract each other so that the imbalance for the rotation in the ψ-direction, and thus the tendency of the irradiation head 102 to free-fall in the rotational direction of ψ may be reduced.

With respect to the rotation of the head section in the ψ-direction, the head support 116 is rotated in this direction by the drive motor 134 through the gear train 136. During this rotation of the head support 116, the cam roller 1088 mounted on the head support 116 pushes down the crosshead 1085 to move it by the displacement which is equal to the Z-component of the displacement of the cam roller 1088. The force applied to the crosshead 1085 from the cam roller 1088 is transmitted through the intermediate wire cable 1074i, the intermediate pulleys 1071u and 1071l, the upper and lower shafts 1070u and 1070l and the side wire cables 1074s to the first balance weights 1040. By virtue of the function of the interlocking mechanism, the displacement of the crosshead 1085 and the associated displacement of the first balance weights 1040 are exactly the same, thereby completely eliminating the imbalance for the rotation in the Φ-direction. The first balance weights 1040 are moved in the opposite direction to the moving direction of the center of gravity of the head section with respect to the Y-axis YA, thereby reducing the imbalance for the rotation in the Φ-direction. Further, the weight of the first balance weights 1040 always acts in the opposite direction to the direction of the tendency of the head section to free-fall so as to rotate about the X-axis, so that the imbalance for the rotation in the ψ-direction can be reduced as well. In addition, since the interlocking mechanism uses the cam mechanism 1084 as an interface between the head section and the wire cable, the conversion of a circular motion into a linear motion can be achieved without any problem of the error between the displacements of the motions to be interlocked, which would be otherwise caused by the loosening of the wire cables.

Thus, according to the irradiation apparatus 1000 of the tenth embodiment, by virtue of the functions of the first movable balance weights 1040 and the third balance weight 1076, as well as the use of the cam mechanism 1084 as an interface, the imbalance for the rotation in the Φ-direction can be completely eliminated, and simultaneously, the imbalance for the rotation in the ψ-direction may be reduced. Thereby the tendency of the head section to free-fall in the ψ-direction may be reduced, and only small capacities are required for the motors 122 and 134 and the gear trains 124 and 136 to drive the head section for rotations in the Φ- and ψ-directions so that they may be of relatively light weight. Further, since the first balance weights 1040 move along paths which are remote from the isocenter ISC, any interference of the first balance weights 1040 with the bed B for a patient can be avoided, and the space under the isocenter ISC is available for better manipulation of the apparatus. In addition, by virtue of the provision of the third balance weight 1076, the initial position of the first balance weights 1040 may be set at a relatively high level, and thus the isocenter ISC may be lowered, so that the manipulability of the apparatus may be further enhanced and the irradiation apparatus may be formed in a more compact configuration.

Figure 23A:
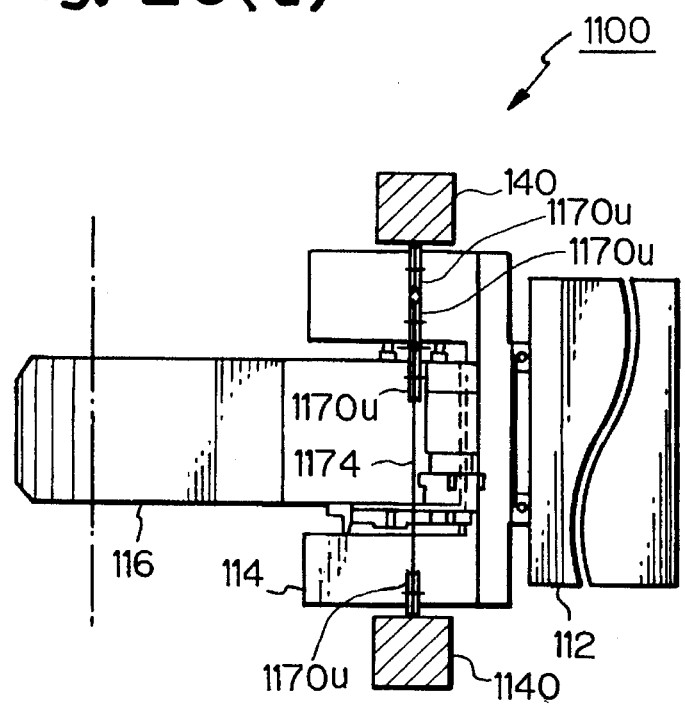
FIG. 23(a) is a top view.
Figure 23B:
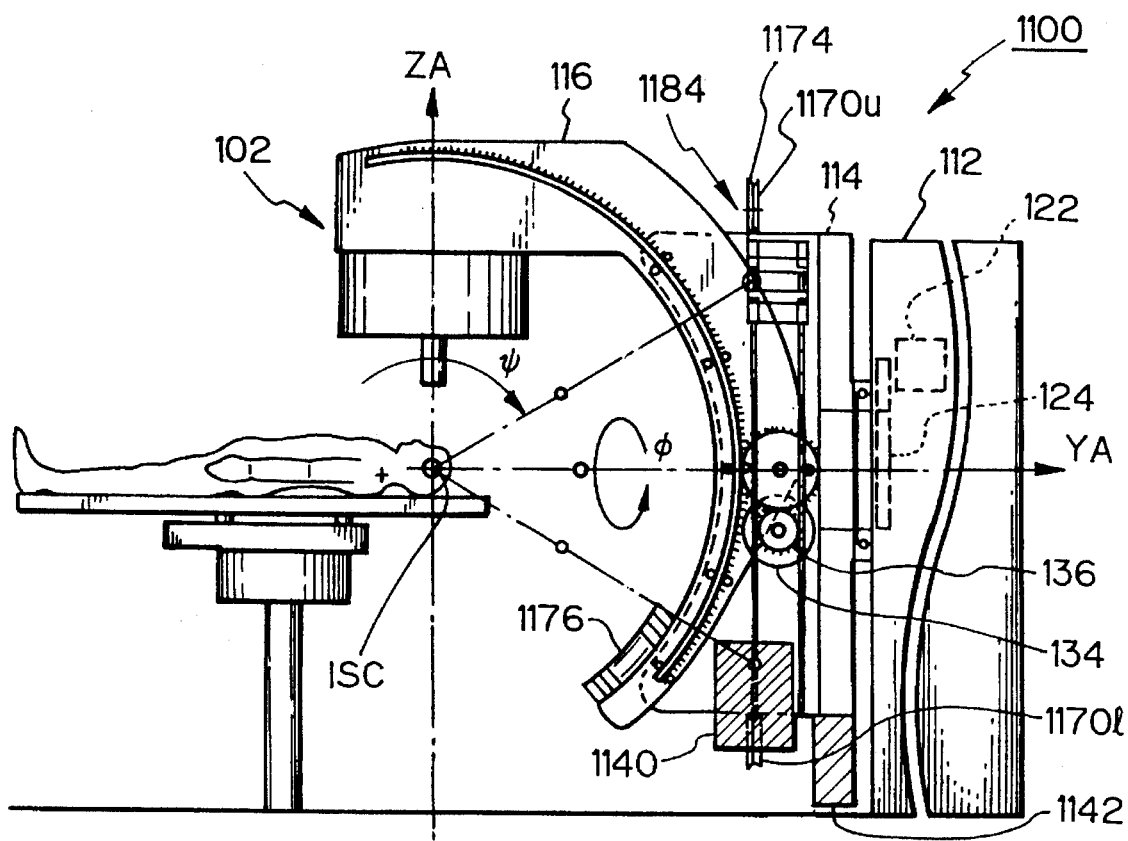
FIG. 23(b) is a side view of an irradiation apparatus in accordance with an eleventh embodiment of the present invention.
Figure 24:
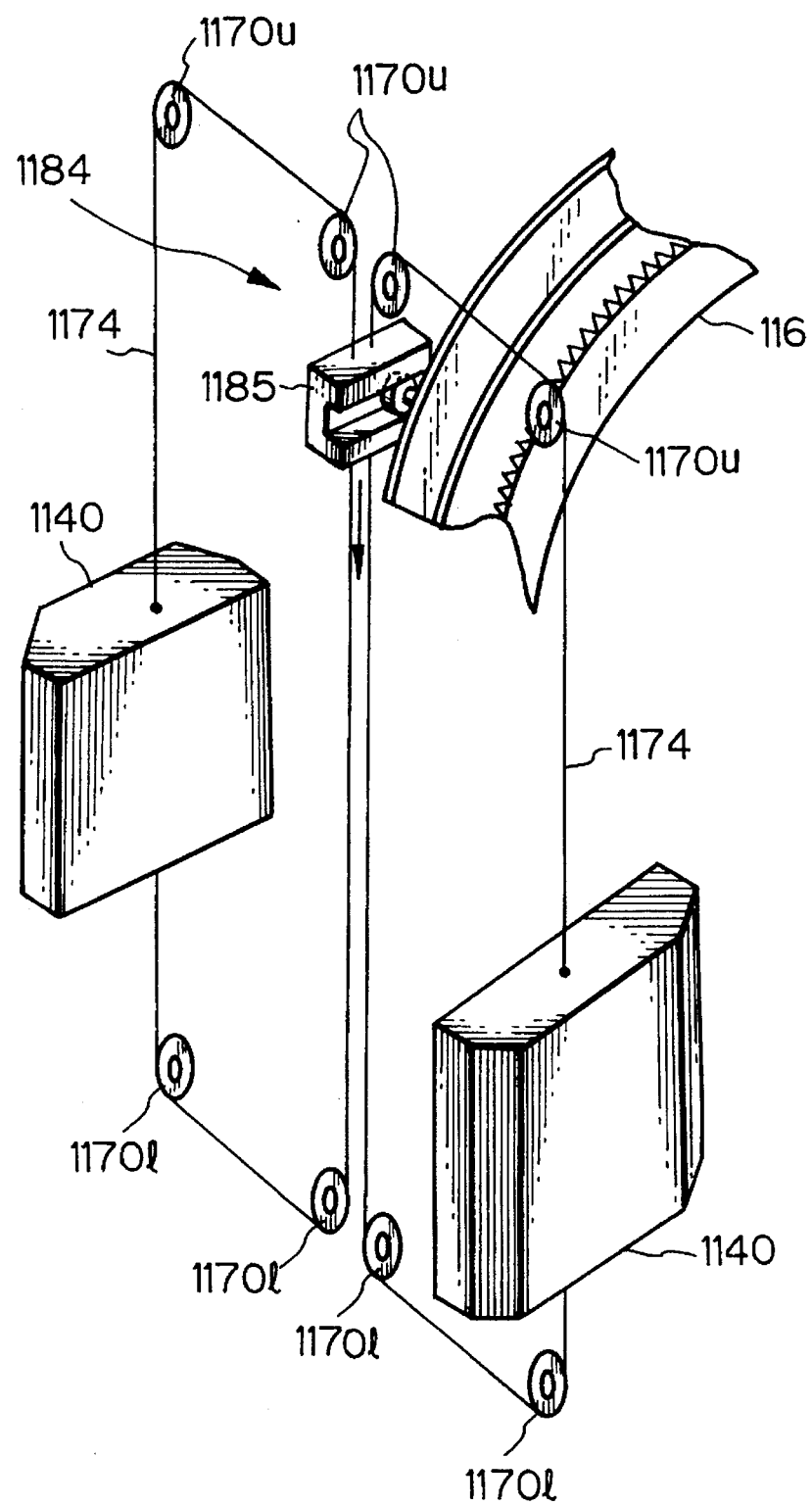
FIG. 24 is an isometric view of the interlocking mechanism used in the irradiation apparatus of FIGS. 23(a) and 23(b)

FIGS. 23 and 24 show an irradiation apparatus 1100 according to an eleventh embodiment of the present invention. FIG. 23(a) is a top view, and FIG. 23(b) is a side view of the apparatus 1100. FIG. 24 is an isometric view of the interlocking mechanism used in the apparatus 1100.

The irradiation apparatus 1100 has a balancing mechanism comprising a pair of first balance weights 1140, a second balance weight 1142 and a third balance weight 1176. The balancing mechanism further comprises an interlocking mechanism for keeping the first balance weights 1140 and the head support 116 in an interlocking relation with each other.

The irradiation apparatus 1100 of the eleventh embodiment is a modification of the irradiation apparatus 1000 of the tenth embodiment. Therefore, only the differences between these embodiments will be described in detail.

The interlocking mechanism of the eleventh embodiment is a wire cable type transmission mechanism comprising two pairs of upper pulleys 1170u which are mounted on the upper portion of the rotary support 114 for rotation, two pairs of lower pulleys 1170l mounted on the lower portion of the rotary support 114 for rotation, and a pair of effectively endless wire cables 1074 each trained on one pair of upper pulleys 1170u and the corresponding one pair of the lower pulleys 1170l and connected to one of the first balance weights 1140. As shown, the upper and lower pulleys 1170u and 1170l have their axes of rotation extending in parallel to the Y-axis YA.

The interlocking mechanism further comprises a cam mechanism 1184 which has the exactly the same structure and the function as the cam mechanism 1084 used in the tenth embodiment described above. However, the crosshead 1185 of the cam mechanism 1184 is connected to both the wire cables 1174.

The irradiation apparatus 1100 of the eleventh embodiment performs the same operation and provides the same function and effect as the irradiation apparatus 1000 of the tenth embodiment described above. However, by virtue of the modification to the interlocking mechanism, and in particular of the arrangement wherein the wire cables 1174 connected to the first balance weights 1140 are directly connected to the cam mechanism 1184, it provides additional advantages that the interlocking mechanism may be formed in a more simple configuration and any error between the positions of the head section and the first balance weights 1140 is completely eliminated, which error could be produced by the slippage between the wire cables and the pulleys if the interlocking mechanism of the tenth embodiment is used and the loosening of the wire cables occur.

Figure 25A:
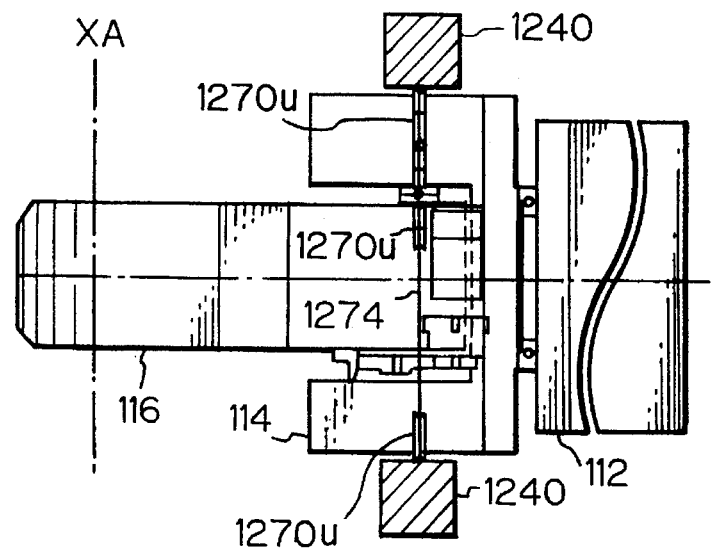
FIG. 25(a) is a top view.
Figure 25B:
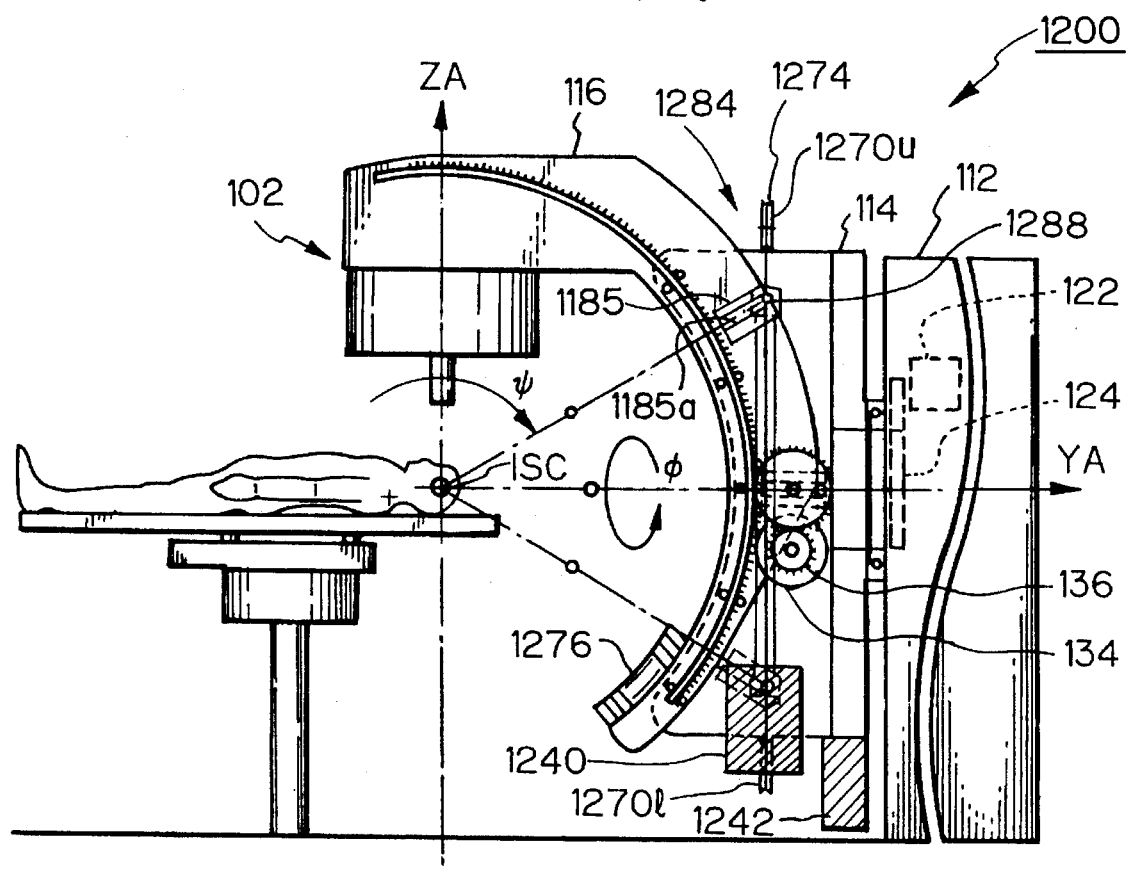
FIG. 25(b) is a side view of an irradiation apparatus in accordance with a twelfth embodiment of the present invention.
Figure 26:
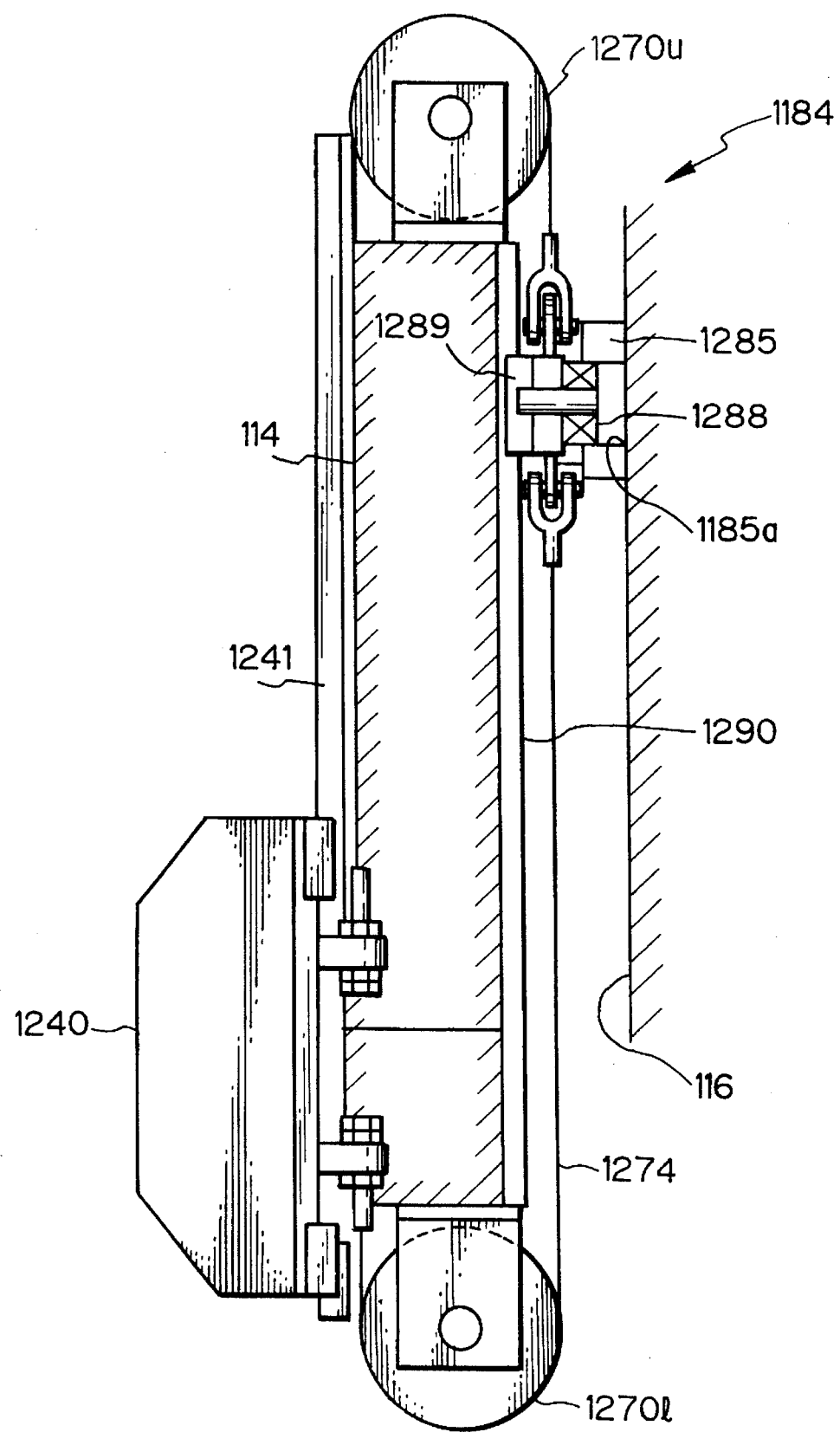
FIG. 26 is a sectional view showing the interlocking mechanism used in the irradiation apparatus of FIGS. 25(a) and 25(b)

FIGS. 25 and 26 shows an irradiation apparatus 1200 according to a twelfth embodiment of the present invention. FIG. 25(a) is a top view, and FIG. 25(b) is a side view of the apparatus 1200. FIG. 26 is a sectional view showing the interlocking mechanism used in the apparatus 1200. Further, FIGS. 26 and 27 will be referred to below for illustration of the operation of the apparatus 1200.

The irradiation apparatus 1200 has a balancing mechanism comprising a pair of first balance weights 1240 (guided by a linear guile unit 1241 (FIG. 26) for linear motion in parallel to the Z-axis), a second balance weight 1242 and a third balance weight 1276. The balancing mechanism further comprises an interlocking mechanism for keeping the first balance weights 1240 and the head support 116 in an interlocking relation with each other.

The irradiation apparatus 1200 of the twelfth embodiment is a further modification of the irradiation apparatus 1100 of the eleventh embodiment. Therefore, only the differences between these embodiments will be described in detail.

The interlocking mechanisms of the eleventh and twelfth embodiments are substantially the same except for the arrangements of their cam mechanisms 1184 and 1284.

The cam mechanism 1284 used in the twelfth embodiment comprises a crosshead 1285 having the same configuration with that of the eleventh embodiment but fixedly mounted on one side of the head support 116 unlike that of the eleventh embodiment. The crosshead 1285 has a guide slot 1285a extending radially with respect to the X-axis XA about which the head support 116 will be rotated.

The cam mechanism 1284 further comprises a cam roller 1288 rotatably mounted on a cam roller carrier 1289 which is connected with the wire cables 1274 and guided by a linear guide unit 1290 mounted on the rotary support 114. The linear guide unit 1290 provides a linear motion of the cam roller carrier 1289, and thus of the cam roller 1288, in parallel to the Z-axis ZA. The cam roller 1288 is in cam-engagement with the guide slot 1285a of the crosshead 1285. When the head support 116 (and thus the head section) is rotated about the X-axis XA, the crosshead 1285 travels along an arcuate path so as to move the cam roller 1288 linearly in parallel to the Z-axis ZA. In this manner, the rotational motion of the head section is converted to a linear motion of the first balance weights 1240.

The irradiation apparatus 1200 of the twelfth embodiment performs the same operation and provides the same function and effect as the irradiation apparatus 1100 of the eleventh embodiment described above. However, by virtue of the modification to the cam mechanism, and in particular of the arrangement wherein the positions of the crosshead and the cam roller is reversed, it provides additional advantages which will be described below in comparison with the eleventh embodiment with reference to FIGS. 27 and 28.

Figure 27:
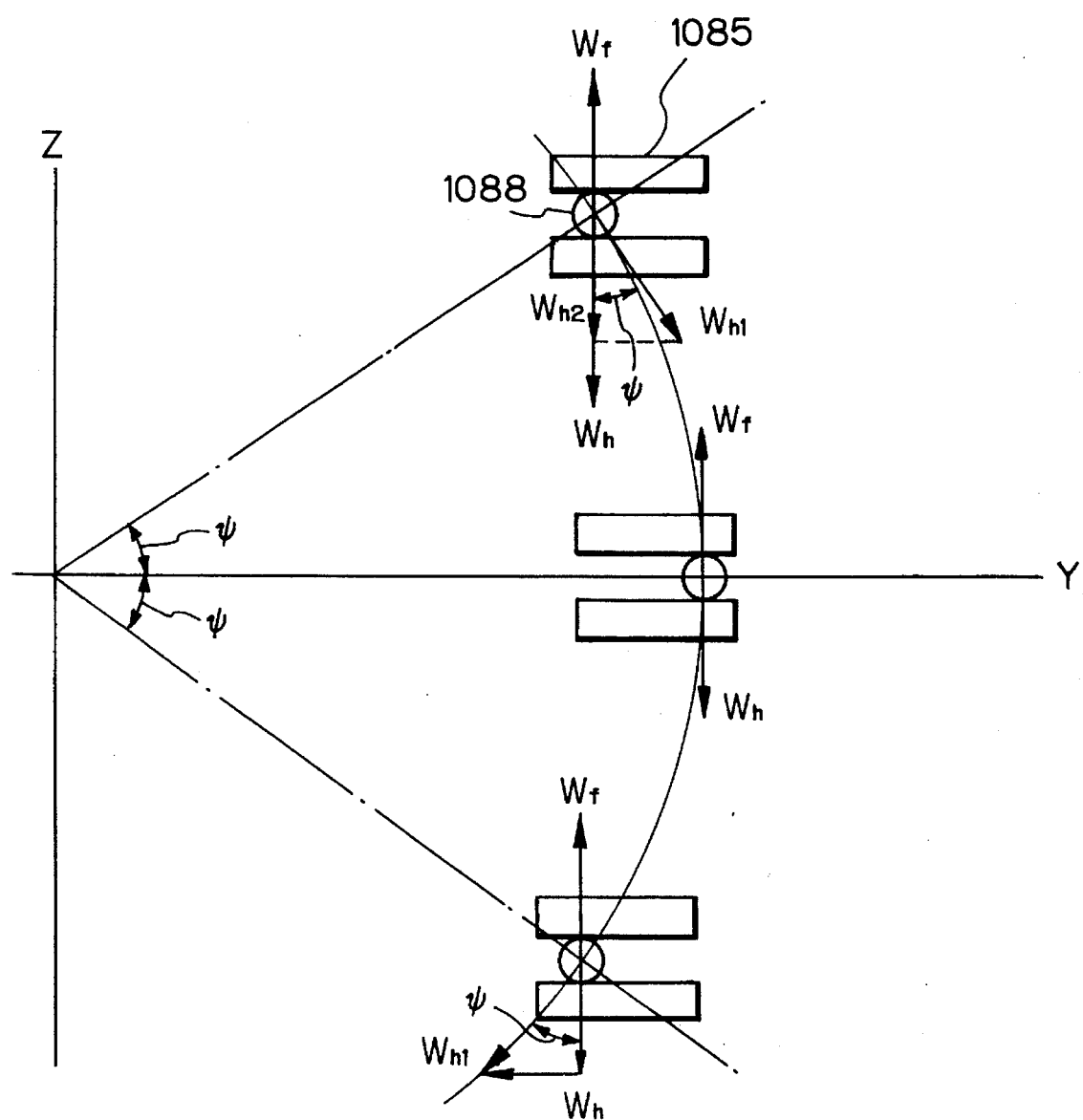
FIG. 27 illustrates the principle of the operation of the irradiation apparatus in accordance with the eleventh embodiment of FIGS. 23(a) and 23(b)

In FIG. 27, which illustrates the operation of the cam mechanism of the eleventh embodiment, $\psi$ represents the rotation angle from the Y-axis in the $\psi$-direction, Wh represents the vertical load of the head section (comprising the head support 116, irradiation head 102 and the third balance weight 1076) acting on the position of the cam roller 1088, Wh1 represents the $\psi$-direction rotational load produced by the rotation of the head section and acting from the cam roller 1088 mounted on the head support 116 onto the crosshead 1085 supported on the rotary support 114, and Wh2 represents the vertical component of the $\psi$-direction rotational load Wh1.

Wf represents the force produced by the first balance weights 1040 tending to lift the head section.

Wh1 and Wh2 are expressed as $$Wh1 = Wh\ \cos\psi$$

$$Wh2 = Wh\ \cos^2\psi.$$

Since the cam roller 1088 always pushes the surface of the crosshead 1085 in perpendicular to the surface, the force Wh2 produced by the weight of the head section and tending to cause the free-fall in the $\psi$-direction rotation varies with the angle $\psi$, while the force produced by the first balance weights 1040 tending to lift the head section is constant. Therefore, the balance when Wh=Wf is expressed as $$Wf - Wh\ \cos^2\psi = Wh\ (1-\cos^2\psi)$$

meaning that the balance will be achieved only when $\psi=0$, otherwise there will be a residual error which amounts to (Wh $(1-\cos^2\psi)$).

Figure 28:
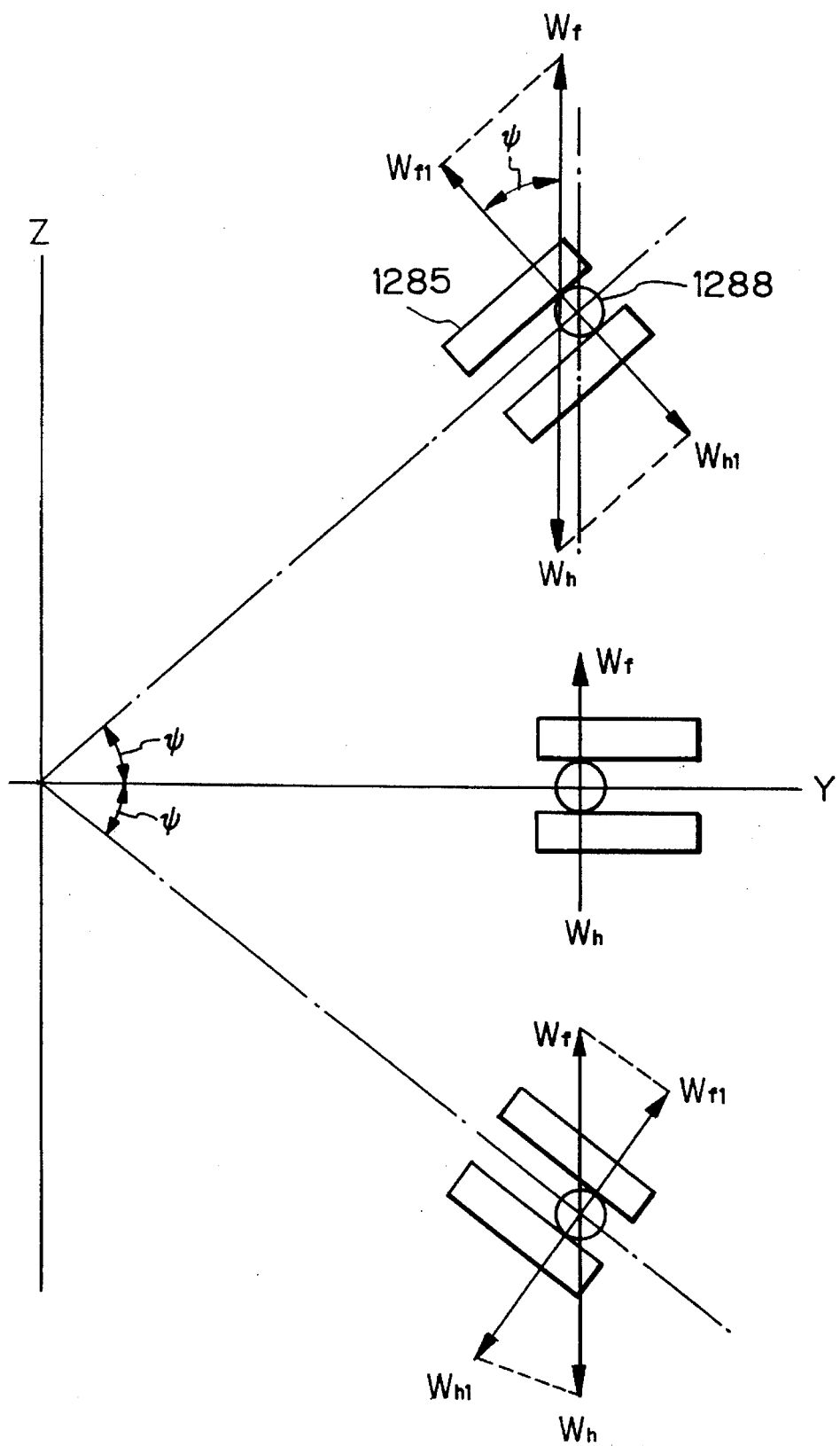
FIG. 28 illustrates the principle of the operation of the irradiation apparatus in accordance with the twelfth embodiment of FIGS. 25(a) and 25(b)

In FIG. 28, which illustrates the operation of the cam mechanism of the twelfth embodiment, the designations Wh, Wh1 and Wf represent the same things as they do in FIG. 27. Additionally, Wf1 represents the pulling force in the rotational direction of $\psi$ produced by the first weights 1240 and acting on the crosshead 1285. Since the crosshead 1285 is fixedly mounted on the head support 116 in this embodiment, the crosshead 1285 will tilt in synchronism with the $\psi$-direction rotation, so that the $\psi$-direction rotation free-fall load Wh1 is expressed as $$Wh1 = Wh\ \cos\psi.$$

On the other hand, the pulling force Wf1 in the rotational direction of $\psi$ produced by the first weights 1240 and acting on the crosshead 1285 is expressed as $$Wf1 = Wf\ \cos\psi.$$

Therefore, if we select as $$Wh = Wf \quad (3)$$

then we have, for any magnitude of $\psi$, $$Wh1 = Wf1$$

meaning that the balance will be achieved.

Further, if we select the Geometry of the interlocking mechanism such that the first balance weights 1240 will be moved in the direction opposite to that of the motion of the crosshead 1285 and by the displacement equal to that of the motion of the crosshead 1285, the balance for the rotation in the $\psi$-direction will be completely achieved.

Therefore, the irradiation apparatus 1200 of the twelfth embodiment provides not only the advantages as shown above in connection with the tenth and eleventh embodiments, but also the additional advantage that both the balances for the rotation in the Φ-direction and the rotation in the $\psi$-direction are completely achieved.

Figure 29A:
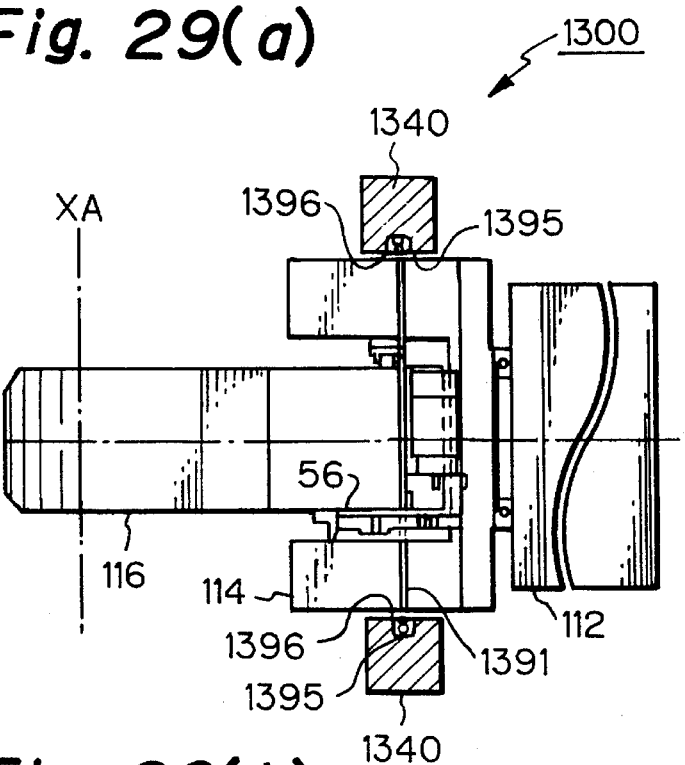
FIG. 29(a) is a top view.
Figure 29B:
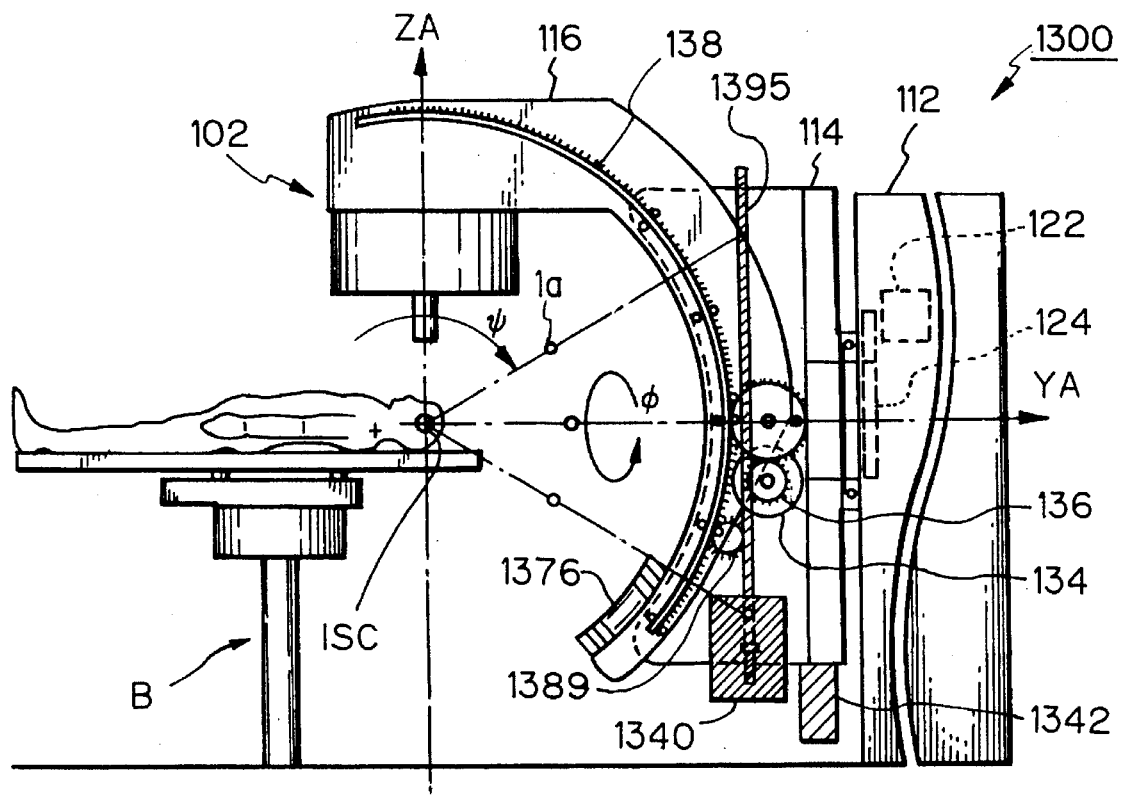
FIG. 29(b) is a side view of an irradiation apparatus in accordance with a thirteenth embodiment of the present invention.
Figure 30:
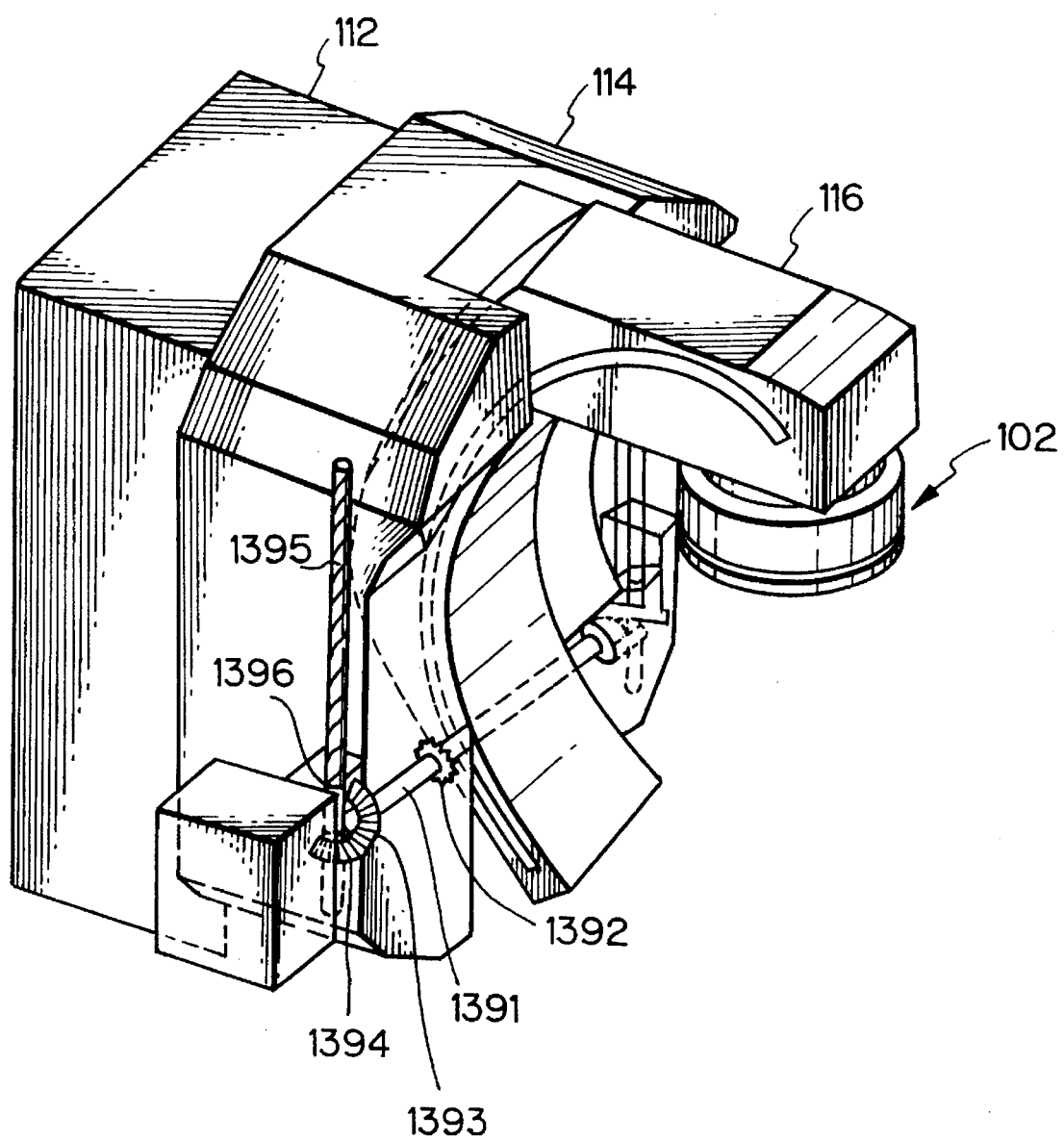
FIG. 30 is an isometric view of the interlocking mechanism used in the irradiation apparatus of FIGS. 29(a) and 29(b)

FIGS. 29 and 30 show an irradiation apparatus 1300 according to a thirteenth embodiment of the present invention. FIG. 29(a) is a top view, and FIG. 29(b) is a side view of the apparatus 1300. FIG. 30 is an isometric view of the interlocking mechanism of the apparatus 1300.

The irradiation apparatus 1300 has a balancing mechanism comprising a pair of first balance weights 1340, a second balance weight 1342 and a third balance weight 1376. The balancing mechanism further comprises an interlocking mechanism for keeping the first balance weights 1340 and the head support 116 in an interlocking relation with each other.

The irradiation apparatus 1300 of the thirteenth embodiment uses the same balancing mechanism as the irradiation apparatus 1300 of the seventh embodiment except that the interlocking mechanism of the thirteenth embodiment is different from that of the seventh embodiment. Corresponding components of the balancing mechanisms of the seventh and thirteenth embodiments are designated by the same reference numerals with the first digit thereof changed from 7 to 13 for the balancing mechanism of the thirteenth embodiment.

The interlocking mechanism is a gear type transmission mechanism comprising a pinion 1389 rotatably mounted on the rotary support 114 and engaging with the arcuate rack 138 fixedly mounted on the head support 116, a shaft 1391 rotatably mounted on the rotary support 114 and extending in parallel to the X-axis, a gear wheel 1392 keyed on the shaft 1391 and engages with the pinion 1389, a pair of first bevel gears 1393 keyed on both ends of the shaft 1391, a pair of second bevel gears 1394 each engaging one of the first bevel gears 1393 and a pair of ball screw and nut mechanisms. Each ball screw and nut mechanism comprises a ball screw 1395 which is rotatable mounted on the rotary support 114, carries one of the second bevel gears 1394 keyed thereon and extends in parallel to the Z-axis ZA, and a nut 1396 cooperating the ball screw 1395 and attached to one of first balance weights 1340. When the head support 116 is rotated, it rotates the shaft 1391 through the arcuate rack 138, the pinion 1389 and the gear wheel 1392, and further rotates the ball screws 1395 through the first and second bevel gears 1393 and 1394 so as to move the nuts 1396 (and thus the first balance weights 1340) up or down depending the rotational direction of the head support 116, and in parallel to the Z-axis ZA.

In operation, the rotary support 114 is rotated in the Φ-direction by the drive motor 122 through the gear train 124, during which the head section (comprising the head support 116, irradiation head 102 and the third balance weight 1376), the second balance weight 1342 and the first balance weights 1340 are rotated in the Φ-direction together. In this rotational motion, the balance for the rotation in the Φ-direction of the head section, the rotary support 114, the second balance weight 942 and the first balance weights 940 is maintained as with the fifth embodiment. Further, with respect to the balance for the rotation in the ψ-direction, the load produced by the weight of the head section and the ψ-direction rotation free-fall force produced by the first balance weights 1340 will counteract each other so that the imbalance for the rotation about X-axis, and thus the tendency of the irradiation head 102 to free-fall in the rotational direction of ψ may be reduced.

With respect to the rotation of the head section in the ψ-direction, the head support 116 is rotated in this direction by the drive motor 134 through the gear train 136. During this rotation of the head support 116, the rotational force or torque is transmitted from the rack 138 fixedly mounted on the head support 116, through the pinion 1389, the gear wheel 1392, the shaft 1391, the first and second bevel gears 1393 and 1394, to the ball screws 1395 to rotate them. The rotations of the ball screws 1395 produce and maintain the thrust forces applied to the nuts 1396 attached to the first balance weights 1340 so as to move the first balance weights 1340 in the opposite direction to the moving direction of the center of gravity of the head section with respect to the Φ-axis, thereby reducing the imbalance for the rotation in the Φ-direction. Further, the weight of the first balance weights 1340 always acts in the opposite direction to the direction of the tendency of the head section to free-fall so as to rotate about the X-axis, so that the imbalance for the rotation in the ψ-direction is reduced as well. In addition, since the circular motion of the head section is converted to the linear motion of the first balance weights 1340 by the interlocking mechanism using a ball screw and nut mechanism, the error between the motions of the head section and the first balance weights 1340 to be interlocked is minimized (which could be produced if a wire cable type interlocking mechanism is used and the loosening of the wire cable occur), so that the imbalances for the rotation in the Φ-direction and the rotation in the ψ-direction may be more reduced than the seventh embodiment.

Thus, according to the irradiation apparatus 1300 of the thirteenth embodiment, by virtue of the functions of the first movable balance weights 1340 and the third balance weight 1376, both the imbalances for the rotation in the Φ-direction and the rotation in the ψ-direction may be more reduced. Thereby the tendency of the head section to free-fall in the rotational direction of ψ is reduced, and only small capacities are required for the motors 122 and 134 and the gear trains 124 and 136 to drive the head section for rotations in the Φ- and ψ-directions so that they may be of relatively light weight. Since the interlocking mechanism for driving the first balance weights 1340 uses a ball screw and nut mechanism, the error of the imbalance may be more reduced. Further, since the first balance weights 1340 move along paths which are remote from the isocenter ISC, any interference of the first balance weights 1340 with the bed B for a patient can be avoided, and the space under the isocenter ISC is available for better manipulation of the apparatus. In addition, by virtue of the provision of the third balance weight 1376, the initial position of the first balance weights 1340 may be set at a relatively high level, and thus the isocenter ISC may be lowered, so that the manipulability of the apparatus may be further enhanced and the irradiation apparatus may be formed in a more compact configuration.

Figure 31A:
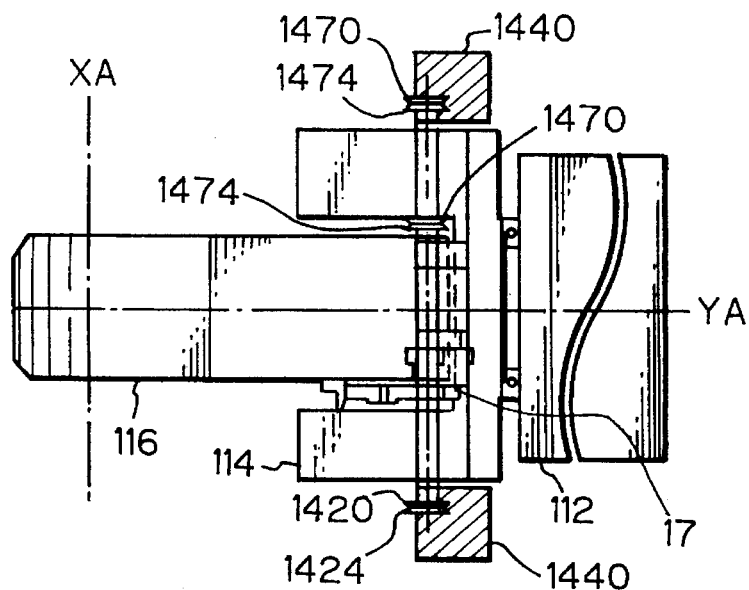
FIG. 31(a) is a top view.
Figure 31B:
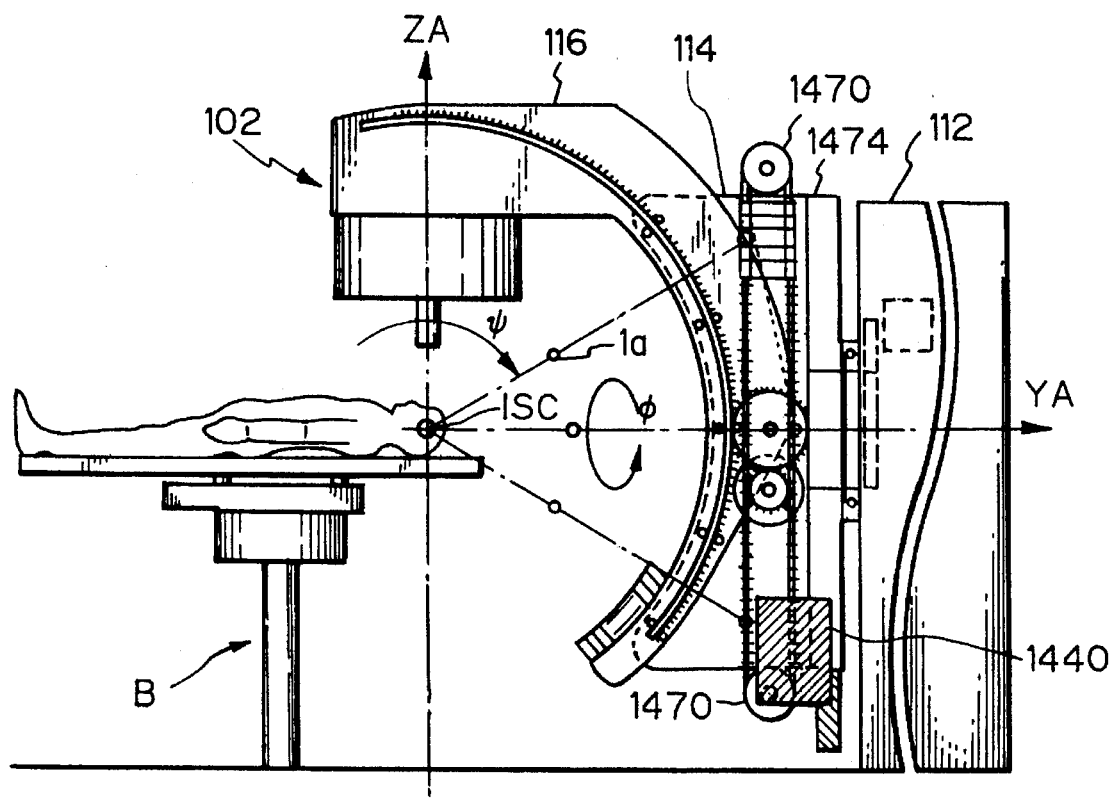
FIG. 31(b) is a side view of an irradiation apparatus in accordance with a fourteenth embodiment of the present invention.

FIG. 31 shows an irradiation apparatus 1400 according to a fourteenth embodiment of the present invention. FIG. 31(a) is a top view, and FIG. 31(b) is a side view of the apparatus 1400.

The irradiation apparatus 1400 has a balancing mechanism comprising a pair of first balance weights 1440, a second balance weight 1442 and a third balance weight 1476. The balancing mechanism further comprises an interlocking mechanism for keeping the first balance weights 1440 and the head support 116 in an interlocking relation with each other. The interlocking mechanism uses a chain type transmission mechanism.

The irradiation apparatus 1400 of the fourteenth embodiment is a modification of the irradiation apparatus 1000 of the tenth embodiment. In fact they are the same except that the wire cables are replaced with the corresponding chains 1474 and the pulleys with the corresponding sprockets 1470. The irradiation apparatus 1400 can perform the same operation and provide the same advantages as the irradiation apparatus 1000 of the tenth embodiment, and further it can provide an additional advantage that any positional error of the first balance weights 1440 is eliminated by the use of the chains in place of the cable wires, which error could occur due to a possible slippage between the wire cable and the associated pulleys.

The above description has been given on various preferred embodiments of the present invention and it will be readily apparent to one skilled in the art that many changes and modifications may be made therein without departing from the spirit and the scope of the present invention. Therefore, scope of the present invention should be determined from the appended claims.

What is claimed is:

1. An irradiation apparatus comprising:
   a) a fixed base;
   b) an irradiation head for projecting a beam of radiation;
   c) support means for supporting said irradiation head, said support means including a first support carried by said fixed base and adapted for rotation about a horizontal first axis, and a second support carried by said first support and adapted for rotation about a second axis which extends perpendicular to said first axis and intersects with said first axis to define an isocenter thereat, said irradiation head being secured to said second support to collectively form a head section;
   d) balance means including a balance weight supported by said first support for rotation about said second axis; and
   e) an interlocking mechanism for operatively interlocking said second support and said balance weight, said interlocking mechanism allowing for curvilinear motion of said balance weight such that said head section and said balance weight have a common center of gravity lying substantially on said first axis.

2. An irradiation apparatus as claimed in claim 1, wherein said interlocking mechanism comprises a gear transmission mechanism.

3. An irradiation apparatus as claimed in claim 1, wherein said interlocking mechanism comprises a wire cable transmission mechanism.

4. An irradiation apparatus as claimed in claim 1, further comprising a second balance weight secured to said first support.

5. An irradiation apparatus comprising:
   a) a fixed base;
   b) an irradiation head for projecting a beam of radiation;
   c) support means for supporting said irradiation head, said support means including a first support carried by said fixed base and adapted for rotation about a horizontal first axis, and a second support carried by said first support and adapted for rotation about a second axis which extends perpendicular to said first axis and intersects with said first axis to define an isocenter thereat, said irradiation head being secured to said second support to collectively form a head section;

d) balance means including a balance weight supported by said first support and linearly moved therealong; and e) an interlocking mechanism for operatively interlocking said second support and said balance weight, said interlocking mechanism allowing for linear motion of said balance weight such that said head section and said balance weight have a common center of gravity lying substantially on said first axis.

6. An irradiation apparatus as claimed in claim 5, wherein said interlocking mechanism comprises a gear transmission mechanism.

7. An irradiation apparatus as claimed in claim 5, wherein said interlocking mechanism comprises a chain transmission mechanism.

8. An irradiation apparatus as claimed in claim 5, further comprising a second balance weight secured to said first support.

9. An irradiation apparatus as claimed in claim 5, wherein said interlocking mechanism comprises a wire cable transmission mechanism.

10. An irradiation apparatus as claimed in claim 9, wherein said wire cable transmission mechanism comprises:

a first wire cable connected to said balance weight;

a first pulley for driving said first wire cable;

a shaft for transmitting a driving force to said first pulley;

a second pulley mounted on said shaft for driving said shaft;

a second wire cable for driving said second pulley; and means for transmitting a driving force from said second support to said wire cable as said second support is rotated.

11. An irradiation apparatus as claimed in claim 10, wherein said wire cable transmission mechanism further includes a tension mechanism for preventing loosening of said wire cables.

12. An irradiation apparatus as claimed in claim 9, wherein said wire transmission mechanism comprises:

a wire cable connected to said balance weight;

a pulley on which said wire cable is trained; and means for transmitting a driving force from said second support to said wire cable when said second support is rotated.

13. An irradiation apparatus as claimed in claim 12, wherein said means for transmitting includes means for converting rotary motion to linear motion.

14. An irradiation apparatus as claimed in claim 13, wherein said means for converting includes a crosshead connected to said wire cable, and a cam member mounted on said second support and engaged with said crosshead.

15. An irradiation apparatus as claimed in claim 13, wherein said means for converting includes a cam member connected to said wire cable, and a crosshead mounted on said second support and engaged with said cam member.

* * * * *